United States Patent
Natan et al.

(10) Patent No.: US 7,225,082 B1
(45) Date of Patent: May 29, 2007

(54) COLLOIDAL ROD PARTICLES AS NANOBAR CODES

(75) Inventors: Michael J. Natan, Los Altos, CA (US); Thomas E. Mallouk, State College, PA (US)

(73) Assignee: Oxonica, Inc., Yarnton Kidlington, Oxfordshire (GB)

( * ) Notice: Subject to any disclaimer, the term of this patent is extended or adjusted under 35 U.S.C. 154(b) by 0 days.

(21) Appl. No.: 09/598,395

(22) Filed: Jun. 20, 2000

Related U.S. Application Data

(60) Provisional application No. 60/194,616, filed on Apr. 5, 2000, provisional application No. 60/190,247, filed on Mar. 17, 2000, provisional application No. 60/189,151, filed on Mar. 14, 2000, and provisional application No. 60/157,326, filed on Oct. 1, 1999.

(51) Int. Cl.
  *B82B 1/00* (2006.01)
  *H01L 29/06* (2006.01)

(52) U.S. Cl. .............................. 702/27; 257/40; 422/50

(58) Field of Classification Search ................ 422/68.1, 422/50; 435/6, 7.1, 4, 7.2; 436/501
See application file for complete search history.

(56) References Cited

U.S. PATENT DOCUMENTS

| | | | |
|---|---|---|---|
| 3,755,730 A | 8/1973 | Vogelgesang | 324/34 R |
| 3,878,367 A | 4/1975 | Fayling et al. | 235/61.12 M |
| 3,897,284 A | 7/1975 | Livesay | 149/21 |
| 4,053,433 A | 10/1977 | Lee | 252/408 |
| 4,098,935 A | 7/1978 | Knudsen | 428/40 |
| 4,131,064 A | 12/1978 | Ryan et al. | 101/1 R |
| 4,306,993 A | 12/1981 | Danielson et al. | 252/316 |
| 4,329,393 A | 5/1982 | La Perre et al. | 428/325 |

(Continued)

FOREIGN PATENT DOCUMENTS

| | | |
|---|---|---|
| EP | 1018365 | 7/2000 |
| WO | WO 97/15390 | 5/1997 |
| WO | WO 99/18240 | 4/1999 |
| WO | WO 00/63419 | 10/2000 |

OTHER PUBLICATIONS

AlMawlawi et al. (1991) J. Appl. Phys. 70(8): 4421–4425.
Al-Rawashdeh et al. (1998) J. Phys. Chem. B 102:361–371.
Braun et al., Nature 402 (1999) 603–604.
Brumlik et al., J. Am. Chem. Soc. 113 (1991) 3174–3175.
Foss et al. (1992) J. Phys. Chem. 96:9001–9007.
Foss et al., J. Phys. Chem. 98 (1994) 2963–2971.
Hornyak et al. (1997) J. Phys. Chem. 101:1548–1555.
Hulteen et al., J. Mater. Chem. 7 (1997) 1075–1087.
Jirage et al. (1997) Science 278:655–658.
Martin (1995) Acc. Chem. Res. 28:61–68.
Nishizawa et al. (1995) Science 268:700–702.
Penner et al. (1987) Anal. Chem. 59:2625–2630.
Sandrock et al. (199) J. Phys. Chem. B 103:11398–11406.
Tierney et al. (1989) J. Phys. Chem. 93:2878–2880.
Liu et al. (1995) Physical Review B, 51(11) 7381–7384.
Piraux et al. (1999) J. Mater. Res., 14(7):3042–3050.
Schwarzacher (1999) Electrochemical Society Interface, 20–24.
Piraux et al. (1994) Applied Physics Letters 65:2484–2486.
Blondel et al. (1994) Applied Physics Letters 65:3019–3021.
Dermody et al. (1999) Abstracts of Papers American Chemical Society 217(1–2) P ANYL 137.
Reiss et al. (1998)) Abstracts of Papers American Chemical Society 216:P173–COLL.

(Continued)

*Primary Examiner*—Marjorie A. Moran
(74) *Attorney, Agent, or Firm*—Swanson & Bratschun L.L.C.

(57) ABSTRACT

Freestanding particles comprising a plurality of segments, wherein the particle length is from 20 nm to 50 μm and the particle width is form 5 nm to 50 μm.

22 Claims, 6 Drawing Sheets

U.S. PATENT DOCUMENTS

| | | | |
|---|---|---|---|
| 4,390,452 A | 6/1983 | Stevens | 252/408.1 |
| 4,397,142 A | 8/1983 | Bingham | 57/238 |
| 4,469,623 A | 9/1984 | Danielson et al. | 252/408.1 |
| 4,527,383 A | 7/1985 | Bingham | 57/200 |
| 4,679,939 A | 7/1987 | Curry et al. | 356/336 |
| 4,855,930 A | 8/1989 | Chao et al. | 364/497 |
| 4,884,886 A | 12/1989 | Salzman et al. | 356/367 |
| 5,091,188 A | 2/1992 | Haynes | 424/450 |
| 5,303,710 A | 4/1994 | Bashkansky et al. | 128/665 |
| 5,449,565 A | 9/1995 | Aoki et al. | 428/694 BA |
| 5,508,164 A | 4/1996 | Kausch et al. | 435/6 |
| 5,512,131 A | 4/1996 | Kumar et al. | 156/655.1 |
| 5,547,748 A | 8/1996 | Ruoff et al. | 428/323 |
| 5,571,726 A | 11/1996 | Brooks et al. | |
| 5,599,615 A * | 2/1997 | Swift et al. | 428/293.1 |
| 5,645,619 A | 7/1997 | Erickson et al. | 51/309 |
| 5,667,667 A | 9/1997 | Southern | 205/687 |
| 5,674,743 A | 10/1997 | Ulmer | 435/287.2 |
| 5,732,150 A | 3/1998 | Zhou et al. | |
| 5,846,517 A | 12/1998 | Unger | 424/9.52 |
| 5,859,700 A | 1/1999 | Yang | |
| 5,927,621 A | 7/1999 | Ziolo et al. | 241/21 |
| 5,985,356 A | 11/1999 | Schultz et al. | 427/8 |
| 5,997,958 A | 12/1999 | Sato et al. | 427/468 |
| 6,020,419 A | 2/2000 | Bock et al. | 524/590 |
| 6,071,336 A | 6/2000 | Fairchild et al. | 106/464 |
| 6,093,302 A | 7/2000 | Montgomery | 205/122 |
| 6,132,278 A * | 10/2000 | Kang et al. | 445/14 |
| 6,143,211 A | 11/2000 | Mathiowitz et al. | 264/4 |
| 6,162,532 A | 12/2000 | Black et al. | 428/323 |
| 6,172,902 B1 | 1/2001 | Wegrowe et al. | |
| 6,334,856 B1 | 1/2002 | Allen et al. | 604/191 |

OTHER PUBLICATIONS

Routkevitch et al. (1996) J Phys Chem 100(33):14037–14045.
Sapp et al. (1999) Chem Mater 11:1183–1185.
Al–Mawlawi et al. (1994) J. Mater. Res. 9:1014.
Bruchez Jr., et al. (1998) Science 281:2013.
Cepak and Martin (1999) Chem. Mater. 11:1363.
Cepak and Martin (1998) J. Phys. Chem. B 102:9985.
Davis et al. (1998) Chem. Mater. 10:2516.
Martin et al. (1999) Adv. Materials 11:1021.
Martin (1996) Chem. Mater. 8:1739.
Meng et al. (1998) Solid State Communications 106:215.
Merchant and Weinberger (2000) Electrophoresis 2000 21:1164.
Michael et al. (1998) Anal. Chem. 70:1242.
van der Zande et al. (1997) J. Phys. Chem. B. 101:852.
Wang et al. (1996) Thin Solid Films 288:86.
Wong et al. (1996) Chem. Mater. 8:2041.
Zhang et al. (1999) Chem. Mater. 11:1659.
McDade and Fulton (1997) Medical Device and Diagnostic Industry 19:75.
Cepak et al. (1997) Chem. Mater. 9:1065.
El–Kouedi et al. (1998) Chem. Mater. 10:3287.
El_Kouedi and Foss, Jr. (2000) J. Phys. Chem. B. 104:4031.
Martin et al. (1990) J. Am. Chem. Soc 112:8976.
Piatek et al. (1998) Nature Biotechnology 16:359.

\* cited by examiner

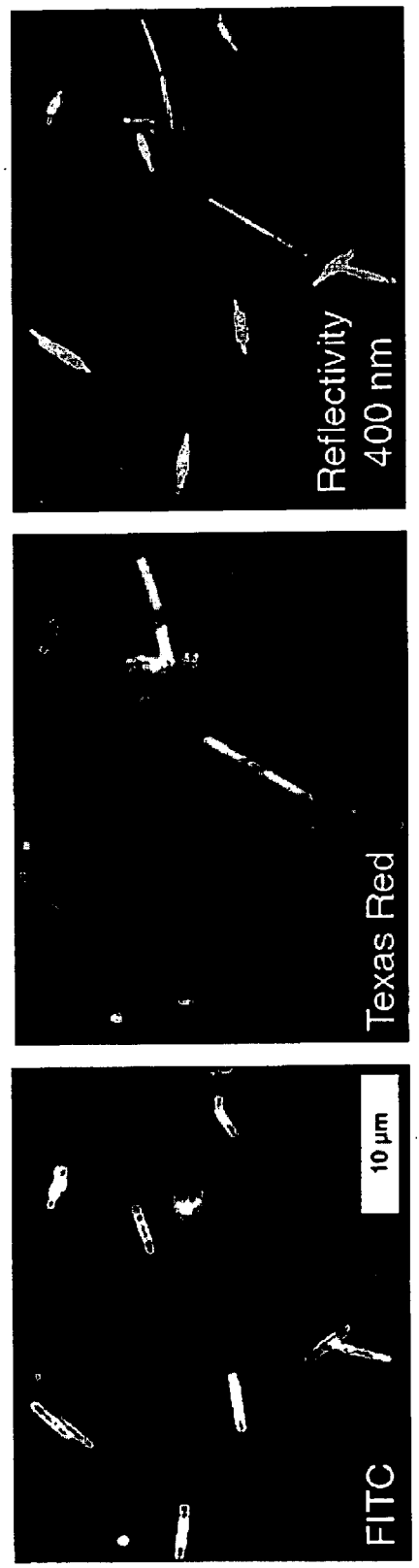
Figure 4A  Figure 4B  Figure 4C 600 nm 400 nm

US 7,225,082 B1

COLLOIDAL ROD PARTICLES AS NANOBAR CODES

RELATED APPLICATIONS

This application claims the benefit of the filing date of U.S. Provisional Application Ser. No. 60/157,326, filed Oct. 1, 1999, entitled "Self Bar-coded Colloidal Metal Nanoparticles"; U.S. Provisional Application Ser. No. 60/189,151, filed Mar. 14, 2000, entitled "Nanoscale Barcodes"; U.S. Provisional Application Ser. No. 60/190,247, filed Mar. 17, 2000, entitled "Colloidal Rod Particles as Barcodes"; and U.S. Provisional Application Ser. No. 60/194,616, filed Apr. 5, 2000, entitled "Nanobarcodes: Technology Platform for Phenotyping."

FIELD OF THE INVENTION

The present invention is directed to nanoparticles, preferably metal, and their methods of manufacture, and methods employing the nanoparticles for a variety of uses. In certain preferred embodiments of the invention, the nanoparticles may be used to encode information and thereby serve as molecular tags or labels.

BACKGROUND OF THE INVENTION

The present invention relates to the composition of matter of segmented particles, assemblies of differentiable particles (which may or may not be segmented) and uses thereof.

Without a doubt, there has been a paradigm change in what is traditionally defined as bioanalytical chemistry. A major focus of these new technologies is to generate what could be called "increased per volume information content". This term encompasses several approaches, from reduction in the volume of sample required to carry out an assay, to highly parallel measurements ("multiplexing"), such as those involving immobilized molecular arrays, to incorporation of second (or third) information channels, such as in 2-D gel electrophoresis or CE-electrospray MS/MS.

Unfortunately, many of these seemingly revolutionary technologies are limited by a DNA microarrays ("gene chips") for analysis of gene expression and genotyping by Affymetrix, Incyte and similar companies has generated the wherewithal to immobilize up to 20,000 different fragments or full-length pieces of DNA in a spatially-defined 1-cm$^2$ array. At the same time, however, the use of these chips in all cases requires hybridization of DNA in solution to DNA immobilized on a planar surface, which is marked both by a decrease in the efficiency of hybridization (especially for cDNA) and a far greater degree of non-specific binding. It is unclear whether these problems can be completely overcome. Moreover, there is a general sense of disillusionment both about the cost of acquiring external technology and the lead-time required to develop DNA arraying internally.

A second example of how groundbreaking can be slowed by inferior tools is in pharmaceutical discovery by combinatorial chemistry. At the moment, solution phase, 5–10 μm diameter latex beads are used extensively as sites for molecular immobilization. Exploiting the widely adopted "split and pool" strategy, libraries of upwards of 100,000 compounds can be simply and rapidly generated. As a result, the bottleneck in drug discovery has shifted from synthesis to screening, and equally importantly, to compound identification, (i.e., which compound is on which bead?). Current approaches to the latter comprise "bead encoding", whereby each synthetic step applied to a bead is recorded by parallel addition of an organic "code" molecule; reading the code allows the identity of the drug lead on the bead to be identified. Unfortunately, the "code reading" protocols are far from optimal: in every strategy, the code molecule must be cleaved from the bead and separately analyzed by HPLC, mass spectrometry or other methods. In other words, there is at present no way to identify potentially interesting drug candidates by direct, rapid interrogation of the beads on which they reside, even though there are numerous screening protocols in which such a capability would be desirable.

Two alternative technologies with potential relevance both to combinatorial chemistry and genetic analysis involve "self-encoded beads", in which a spectrally identifiable bead substitutes for a spatially defined position. In the approach pioneered by Walt and co-workers, beads are chemically modified with a ratio of fluorescent dyes intended to uniquely identify the beads, which are then further modified with a unique chemistry (e.g. a different antibody or enzyme). The beads are then randomly dispersed on an etched fiber array so that one bead associates with each fiber. The identity of the bead is ascertained by its fluorescence readout, and the analyte is detected by fluorescence readout at the same fiber in a different spectral region. The seminal paper (Michael et al., Anal. Chem. 70, 1242–1248 (1998)) on this topic points out that with 6 different dyes (15 combinations of pairs) and with 10 different ratios of dyes, 150 "unique optical signatures" could be generated, each representing a different bead "flavor". A very similar strategy is described by workers at Luminex, who combine flavored beads ready for chemical modification (100 commercially available) with a flow cytometry-like analysis. (See, e.g., McDade et al., Med. Rev. Diag. Indust. 19, 75–82 (1997)). Once again, the particle flavor is determined by fluorescence, and once the biochemistry is put onto the bead, any spectrally distinct fluorescence generated due to the presence of analyte can be read out. Note that as currently configured, it is necessary to use one color of laser to interrogate the particle flavor, and another, separate laser to excite the bioassay fluorophores.

A more significant concern with self-encoded latex beads is the limitations imposed by the wide bandwidth associated with molecular fluorescence. If the frequency space of molecular fluorescence is used both for encoding and for bioassay analysis, it is hard to imagine how, for example, up to 20,000 different flavors could be generated. This problem might be alleviated somewhat by the use of combinations of glass-coated quantum dots, which exhibit narrower fluorescence bandwidths. (See, e.g. Bruchez et al., Science, 2, 2013–2016 (1998)). However, these "designer" nanoparticles are quite difficult to prepare, and at the moment, there exist more types of fluorophores than (published) quantum dots. Moreover, how to combine multiple quantum dots into a "superparticle" that could serve as an encoding element has apparently not yet been demonstrated. If, however, it were possible to generate very large numbers of intrinsically-differentiable particles by some means, then particle-based bioanalysis would become exceptionally attractive, insofar as a single technology platform could then be considered for the multiple high-information content research areas; including combinatorial chemistry, genomics, and proteomics (via multiplexed immunoassays).

Previous work has originally taught how metal can be deposited into the pores of a metallized membrane to make an array of metal nanoparticles embedded in the host. Their focus was on the optical and/or electrochemical properties of these materials. A similar technique was used to make segmented cylindrical magnetic nanoparticles in a host membrane, where the composition of the particles was varied along the length. In no case, however, have freestanding, rod-shaped nanoparticles with variable compositions along their length been prepared. Indeed, "freestanding" rod-shaped metal nanoparticles of a single composition, in which the length is at least one micron, have never been reported. Likewise, freestanding rod-shaped metal nanoparticles not embedded or otherwise contained within such host materials have never been reported.

SUMMARY OF THE INVENTION

Rod-shaped nanoparticles have been prepared whose composition is varied along the length of the rod. These particles are referred to as nanoparticles or nanobar codes, though in reality some or all dimensions may be in the micron size range.

The present invention includes free-standing particles comprising a plurality of segments, wherein the particle length is from 20 nm to 50 µm and particle width is from 5 nm to 50 µm. The segments of the particles of the present invention may be comprised of any material. Included among the possible materials are a metal, any metal chalcogenide, a metal oxide, a metal sulfide, a metal selenide, a metal telluride, a metal alloy, a metal nitride, a metal phosphide, a metal antimonide, a semiconductor, a semi-metal, any organic compound or material, any inorganic compound or material, a particulate layer of material or a composite material. The segments of the particles of the present invention may be comprised of polymeric materials, crystalline or non-crystalline materials, amorphous materials or glasses. In certain preferred embodiments of the invention, the particles are "functionalized" (e.g., have their surface coated with IgG antibody). Such functionalization may be attached on selected or all segments, on the body or one or both tips of the particle. The functionalization may actually coat segments or the entire particle. Such functionalization may include an organic compound, such as an antibody, an antibody fragment, or an oligonucleotide. Such functionalization may also be a detectable tag or comprise a species that will bind a detectable tag.

Also included within the present invention is an assembly or collection of particles comprising a plurality of types of particles, wherein each particle is from 20 nm to 50 µm in length and is comprised of a plurality of segments, and wherein the types of particles are differentiable. In the preferred embodiments, the particle types are differentiable based on differences in the length, width or shape of the particles and/or the number, composition, length or pattern of said segments. In other embodiments, the particles are differentiable based on the nature of their functionalization.

The present invention also includes a composition comprised of a particle and a functional unit (e.g., an IgG antibody on the surface) wherein said particle comprises a plurality of segments and has a length of 20 nm to 50 µm. In certain embodiments the specific nature of the functional unit is encoded by the particle, preferably based on the length, width or shape of the particle and/or the number, composition, length or pattern of segments.

The present invention includes an assembly of particles comprising a plurality of types of particles wherein each particle has at least one dimension of less than 1 µm, and wherein the types of particles are differentiable. Preferably, the types of particles are differentiable based on the length, width, shape and/or composition of the particles. Further included in the invention are compositions comprised of a particle and a functional unit wherein said particle has at least one dimension of less than 1 µm, and wherein the nature of the functional unit is encoded by the particle.

The present invention includes a method for encoding information about a material or product (e.g., paint, rubber, metal, wood, textiles, gunpowder, paper, plastics, glass, etc.) comprising incorporating within or attaching to said material or product a free standing particle that encodes the information, said particle comprising a plurality of segments, wherein the particle length is from 20 nm to 50 µm and the particle width is from 5 nm to 50 µm; and wherein said encoded information is based on the length, width or shape of the particle and/or the number, composition, length or pattern of the segments.

Methods for conducting an assay or measurement of analyte concentration or activity are also included within the invention. Such methods include contacting a solution that may contain said analyte with a composition comprising a molecule, species or material that interacts with said analyte bound to a particle comprising a plurality of segments, wherein said particle length is from 20 nm to 50 µm and the particle width is from 5 nm to 50 µm; and detecting whether an interaction has occurred.

Methods are also taught for simultaneously conducting a plurality of assays or measurements of analyte concentrations or activities to a plurality of analytes comprising contacting a solution that may contain said analytes with a plurality of compositions, wherein each composition comprises a molecule, species or material that interacts with one of said analytes bound to a particle comprising a plurality of segments; wherein the particle length is from 20 nm to 50 m and the particle width is from 5 nm to 50 µm; and wherein the nature of said compositions is encoded by the particle to which it is bound; and detecting which interactions have occurred.

BRIEF DESCRIPTION OF THE FIGURES

FIG. 4 demonstrates simultaneous bar code detection by reflectivity and analyte quantitation by fluorescence. Each of the images is of a mixture of striped nanorods, as described in Example 4. FIG. 4A is imaged at the wavelength of FITC emission with a bandpass filter. FIG. 4B is imaged at the wavelength of Texas Red. FIG. 4C is a reflectivity image at 400 nm.

DETAILED WRITTEN DESCRIPTION OF THE INVENTION

Figure 1A:
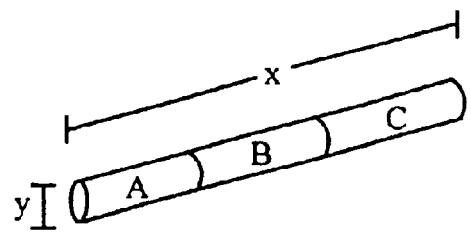
FIGS. 1A–1D depict schematically 4 different illustrative nanoparticles of the present invention.
Figure 1B:
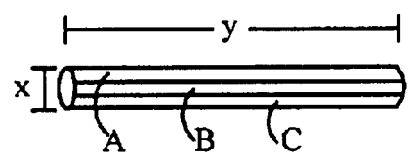
Figure 1C:
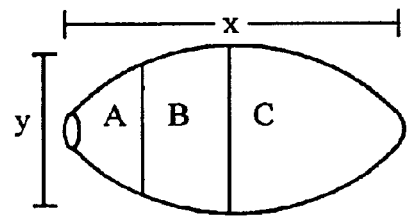
Figure 1D:
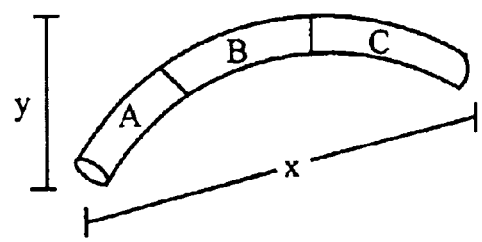

Because bar coding is so widely-used in the macroscopic world, the concept has been translated to the molecular world in a variety of figurative manifestations. Thus, there are "bar codes" based on analysis of open reading frames, bar codes based on isotopic mass variations, bar codes based on strings of chemical or physical reporter beads, bar codes based on electrophoretic patterns of restriction-enzyme cleaved mRNA, bar-coded surfaces for repeatable imaging of biological molecules using scanning probe microscopies, and chromosomal bar codes (a.k.a. chromosome painting) produced by multi-chromophore fluorescence in situ hybridization. All these methods comprise ways to code biological information, but none offer the range of advantages of the bona fide bar codes of the present invention, transformed to the nanometer scale.

The particles of the present invention are alternately referred to as nanoparticles, nanobar codes, rods and rod shaped particles. To the extent that any of these descriptions may be considered as limiting the scope of the invention, the label applied should be ignored. For example, although in certain embodiments of the invention, the particle's composition contains informational content, this is not true for all embodiments of the invention. Likewise, although nanometer-sized particles fall within the scope of the invention, not all of the particles of the invention fall within such size range.

In preferred embodiments of the present invention, the nanobar code particles are made by electrochemical deposition in an alumina or polycarbonate template, followed by template dissolution, and typically, they are prepared by alternating electrochemical reduction of metal ions, though they may easily be prepared by other means, both with or without a template material. Typically, the nanobar codes have widths between 30 nm and 300 nanometers, though they can have widths of several microns. Likewise, while the lengths (i.e. the long dimension) of the materials are typically on the order of 1 to 15 microns, they can easily be prepared in lengths as long as 50 microns, and in lengths as short as 20 nanometers. In some embodiments, the nanobar codes comprise two or more different materials alternated along the length, although in principle as many as dozens of different materials could be used. Likewise, the segments could consist of non-metallic material, including but not limited to polymers, oxides, sulfides, semiconductors, insulators, plastics, and even thin (i.e., monolayer) films of organic or inorganic species.

When the particles of the present invention are made by electrochemical deposition the length of the segments can be adjusted by controlling the amount of current passed in each electroplating step; as a result, the rod resembles a "bar code" on the nanometer scale, with each segment length (and identity) programmable in advance. The same result could be achieved using another method of manufacture in which the length or other attribute of the segments can be controlled. While the diameter of the rods and the segment lengths are typically of nanometer dimensions, the overall length is such that in preferred embodiments it can be visualized directly in an optical microscope, exploiting the differential reflectivity of the metal components.

The term bar code is appropriate because, for example, rods with 9 segments have been prepared, as have particles with segments comprised of 4 different materials (each with a different reflectivity). Thus, for this example, there are $4^9$ (>260,000) unique types of bar code nanoparticles that could potentially be prepared. When one considers that particle diameter or width, segment length and overall particle length can be varied, and that there are a huge number of additional materials that can be added to those already available, there are actually many more. The point is that there are literally billions of unique (and identifiable) compositions of matter.

A second key feature of the bar code nanoparticles is that the full range of chemical surface functionalization can be applied to the nanoparticle surface, including, but not limited to, functionalization with self assembled monolayers (SAMs), polymers, oxides, other metals, nucleic acids, proteins, lipids and combinations thereof. Accordingly, they can be used for supports for sensors based on fluorescence (the metal surfaces do not quench the fluorescence of surface-confined molecules), and can also form a highly novel active sensor element based on reflectivity changes. Because any sensor configuration can be translated to the nanobar code surface, detection can also be accomplished by electrochemical, mass spectrometric, gravimetric, optical, mechanical and numerous other methods. It is important to note that because the rods are, to a first approximation, a 1-D structure, solvent access to immobilized biomolecules is significantly enhanced relative to a sphere of the same linear dimension, and especially relative to planar surfaces. This can be easily verified, for example, by inspection of the mass transport equations to hemispherical and semi-infinite cylindrical microelectrodes and for macroscopic planar electrodes. Thus, especially for the narrower bars, molecular recognition reactions will behave much like their solution counterparts. For the same reason, non-specific binding should be significantly reduced: the total surface area, for example, of a 200-nm width, 3-μm length rod is <0.1 μm². In short, cylindrically-shaped nanoparticles offer surface properties that are useful for bioassay construction.

The synthesis and characterization of multiple segmented particles is described in Martin et al., Adv. Materials 11:1021–25 (1999). The article is incorporated herein by reference in its entirety. Also incorporated herein by reference in their entirety are U.S. Provisional Application Ser. No. 60/157,326, filed Oct. 1, 1999, entitled "Self Bar-coded Colloidal Metal Nanoparticles"; U.S. Provisional Application Ser. No. 60/189,151, filed Mar. 14, 2000, entitled "Nanoscale Barcodes"; U.S. Provisional Application Ser. No. 60/190,247, filed Mar. 17, 2000, entitled "Colloidal Rod Particles as Barcodes"; and U.S. Provisional Application Ser. No. 60/194,616, filed Apr. 5, 2000, entitled "Nanobarcodes: Technology Platform for Phenotyping."

In describing the scope of the particles of the present invention, reference should be made to FIG. 1. This figure depicts diagramatically 4 non-limiting possible shapes of the nanobar codes of the present invention. In these diagrams, each of the particles is comprised of 3 segments, A, B and C, and the dimension defined as the length is denoted x and the dimension defined as the width is denoted y. In each of these embodiments, the length is defined as the axis that runs generally perpendicular to lines defining the segment transitions, while the width is the dimension of the particle that runs parallel to the line defining the segment transitions. As can be seen in FIG. 1C, the particle width can vary across the length of the particle, and in the same way the particle length may vary across the width of the particle. As can be seen in FIG. 1D, the particles of the present invention may be curved. Other possible shapes of the particles of the present invention include branched, t-shaped or even donut-shaped particles. In such embodiments, it may be convenient to refer to the largest dimension of the particles as its length and a shorter, roughly perpendicular dimension as the width. The particles of the present invention are defined in part by their size and by the existence of at least 2 segments. The length of the particles can be from 20 nm up to 50 μm. In preferred embodiments the particle is 500 nm–30 μm. In the most preferred embodiments, the length of the particles of this invention is 1–15 μm.

The particles of the invention are frequently referred to as being "rod" shaped. However, the cross-sectional shape of the particles, viewed along the long axis, can have any shape, and can change at different portions of the particle. Such cross-sections may be a circle, an oval, square, diamond or even tubular. In preferred embodiments of the invention, the cross section is a circle and the particles are "rod" shaped. Although the particles of the present invention may take many shapes, the segmented particles of the present invention are not spherical.

The width, or diameter, of the particles of the invention is within the range of 5 nm–50 μm. In preferred embodiments the width is 10 nm–1 μm, and in the most preferred embodiments the width or cross-sectional dimension is 30 nm–500 nm.

As discussed above, the particles of the present invention are characterized by the presence of at least two segments. A segment represents a region of the particle that is distinguishable, by any means, from adjacent regions of the particle. Referring to FIG. 1A, segments of the particle bisect the length of the particle to form regions that have the same cross-section (generally) and width as the whole particle, while representing a portion of the length of the whole particle. In preferred embodiments of the invention, a segment is composed of different materials from its adjacent segments. However, not every segment needs to be distinguishable from all other segments of the particle. For example, a particle could be composed of 2 types of segments, e.g., gold and platinum, while having 10 or even 20 different segments, simply by alternating segments of gold and platinum. A particle of the present invention contains at least two segments, and as many as 50. The particles of the invention preferably have from 2–30 segments and most preferably from 3–20 segments. The particles may have from 2–10 different types of segments, preferably 2 to 5 different types of segments.

A segment of the particle of the present invention is defined by its being distinguishable from adjacent segments of the particle. The ability to distinguish between segments includes distinguishing by any physical or chemical means of interrogation, including but not limited to electromagnetic, magnetic, optical, spectrometric, spectroscopic and mechanical. In certain preferred embodiments of the invention, the method of interrogating between segments is optical (reflectivity).

Adjacent segments may even be of the same material, as long as they are distinguishable by some means. For example, different phases of the same elemental material, or enantiomers of organic polymer materials can make up adjacent segments. In addition, a rod comprised of a single material could be considered to fall within the scope of the invention if segments could be distinguished from others, for example, by functionalization on the surface, or having varying diameters. Also particles comprising organic polymer materials could have segments defined by the inclusion of dyes that would change the relative optical properties of the segments.

The composition of the particles of the present invention is best defined by describing the compositions of the segments that make up the particles. A particle may contain segments with extremely different compositions. For example, a single particle could be comprised of one segment that is a metal, and a segment that is an organic polymer material.

The segments of the present invention may be comprised of any material. In preferred embodiments of the present invention, the segments comprise a metal (e.g., silver, gold, copper, nickel, palladium, platinum, cobalt, rhodium, iridium); any metal chalcognide; a metal oxide (e.g., cupric oxide, titanium dioxide); a metal sulfide; a metal selenide; a metal telluride; a metal alloy; a metal nitride; a metal phosphide; a metal antimonide; a semiconductor; a semimetal. A segment may also be comprised of an organic mono- or bilayer such as a molecular film. For example, monolayers of organic molecules or self assembled, controlled layers of molecules can be associated with a variety of metal surfaces.

A segment may be comprised of any organic compound or material, or inorganic compound or material or organic polymeric materials, including the large body of mono and copolymers known to those skilled in the art. Biological polymers, such as peptides, oligonucleotides and carbohydrides may also be the major components of a segment. Segments may be comprised of particulate materials, e.g., metals, metal oxide or organic particulate materials; or composite materials, e.g., metal in polyacrylamide, dye in polymeric material, porous metals. The segments of the particles of the present invention may be comprised of polymeric materials, crystalline or non-crystalline materials, amorphous materials or glasses.

Segments may be defined by notches on the surface of the particle, or by the presence of holes or perforations into the particle. In embodiments of the invention where the particle is coated, for example with a polymer or glass, the segment may consist of a void between other materials.

The length of each segment may be from 10 nm to 50 μm. In preferred embodiments the length of each segment is 50 nm to 20 μm. As depicted in FIG. 1, the juncture between segments is represented as a clean cross sectional interface. However, the interface between segments, in certain embodiments, need not be perpendicular to the length of the particle or a smooth line of transition. In addition, in certain embodiments the composition of one segment may be blended into the composition of the adjacent segment. For example, between segments of gold and platinum, there may be a 5 to 50 nm region that is comprised of both gold and platinum. This type of transition is acceptable so long as the segments are distinguishable. For any given particle the segments may be of any length relative to the length of the segments of the rest of the particle.

As described above, the particles of the present invention can have any cross-sectional shape. In preferred embodiments, the particles are generally straight along the lengthwise axis. However, in certain embodiments the particles may be curved or helical. The ends of the particles of the present invention may be flat, convex or concave. In addition, the ends may be spiked or pencil tipped. Sharp-tipped embodiments of the invention may be preferred when the particles are used in Raman spectroscopy applications or others in which energy field effects are important. The ends of any given particle may be the same or different.

In many embodiments of the invention, an assembly or collection of particles is prepared. In certain embodiments, the members of the assembly are identical, while in other embodiments, the assembly is comprised of a plurality of different types of particles. In embodiments of the invention comprising assemblies of identical particles, the length of particles for particles in the 1 μm–15 μm range may vary up to 10%. Segments of 10 nm in length will vary ±5 nm while segments in 1 μm range may vary up to 10%. The width of such particles may vary between 10 and 100% preferably less than 50% and most preferably less than 10%.

The present invention includes assemblies or collections of nanobar codes made up of a plurality of particles that are differentiable from each other. Assembly or collection, as used herein, does not mean that the nanoparticles that make up such an assembly or collection are ordered or organized in any particular manner. Such an assembly is considered to be made up of a plurality of different types or "flavors" of particles. In some such assemblies, each of the nanobar codes of the assembly may be functionalized in some manner. In many applications, the functionalization is different and specific to the specific flavor of nanoparticle. The assemblies of the present invention can include from 2 to $10^{10}$ different and identifiable nanoparticles. Preferred assemblies include more than 10, more than 100, more than 1,000 and, in some cases, more than 10,000 different flavors of nanoparticles. The particles that make up the assemblies or collections of the present invention are segmented in most embodiments. However, in certain embodiments of the invention the particles of an assembly of particles do not necessarily contain a plurality of segments.

In the embodiments of the present invention where the nanobar codes contain some informational content, or where an assembly of nanobar codes contain a plurality of types of particles, the types of particles are differentiable apart from the nature of the functionalization of each particle type. In this invention, the ability to differentiate particle types or to interpret the information coded within a particle is referred to as "interrogating" or "reading" or "differentiating" or "identifying" the nanoparticle. Such differentiation of particles may be read by any means, including optical means, electronic means, physical means, chemical means and magnetic means. The particle may even contain different sections that will be interrogated or read by different means. For example, one half of a particle may be comprised of segments whose pattern and shapes can be read by optical means, and the other half may be comprised of a segment whose pattern and shapes may be read by magnetic means. In another example, two different forms of interrogation may be applied to an entire particle, e.g., the shape or length of the particle may be read by optical means and the segment patterns by magnetic means.

In many embodiments of the present invention, one or more segments of the particle, the ends of the particle, or the entire particle may be functionalized. By functionalization, or attachment of a functional unit, it is meant that some species or material is covalently or noncovalently attached to the surface of the particle. Examples of functionalization include the attachment, often via a linker, to an antibody or antibody fragment, to an oligonucleotide or a to a detectable tag. In some embodiments, the particles of the invention are multiply functionalized. As used herein, the term functional unit is meant to define any species that modifies, attaches to, appends from, coats or is covalently or non-covalently bound to the surface of any portion of the nanobar code particle.

Functionalization of the particles of the present invention may take many forms. Functionalization is defined herein as any modification of the surface of the particle as covalently or non-covalently modified, derivatized, or otherwise coated with an organic, inorganic, organometallic or composition monolayer, multilayer, film, polymer, glass, ceramic, metal, semi-metal, semiconductor, metal oxide or metal chalcogenide. Such functionalization may occur on individual segments, e.g., a gold and silver particle may be functionalized on the gold and not the silver, or the gold may be functionalized in one manner while the silver is differently functionalized.

In other embodiments, the entire particle may be coated with the same substance or only certain segments of the particle will be coated. Such coatings may be comprised of any material. In embodiments of the invention where the particles of the invention are coated, and separations occur by differential absorption/desorption from the coating material, the functionalization coating or film may comprise any organic functional group, including but not limited to, acids, amines, thiols, ethers, esters, thioesters, thioethers, carbamates, amides, thiocarbonates, dithiocarbonates, imines, alkenes, alkanes, alkynes, aromatic groups, alcohols, heterocycles, cyanates, isocyanates, nitrites, isonitriles, isothiocyanates, and organocyanides. The coating or functionalization may comprise any inorganic coordination complex, including but not limited to 2-, 3-, 4-, 5-, 6-, 7-, 8- and 9- coordinate complexes. The coating or functionalization may comprise any organometallic complex, including but not limited to species containing one or more metal-carbon, metal-silicon, or metal nitrogen bonds. In addition, the coatings or functionalization of the particles of the present invention may comprise any combination of organic functional groups, inorganic or organometallic species.

The functionalization of the particles of the present invention may occur on the entire particle, on selected segments or in certain embodiments, on the tips or ends of the particles. In such embodiment, both or just one of the tips may be functionalized, and the nature of the functionalization may differ at the tips.

In certain embodiments of the invention, the functional unit or functionalization of the particle comprises a detectable tag. A detectable tag is any species that can be used for detection, identification, enumeration, tracking, location, positional triangulation, and/or quantitation. Such measurements can be accomplished based on absorption, emission, generation and/or scattering of one or more photons; absorption, emission generation and/or scattering of one or more particles; mass; charge; faradoic or non-faradoic electrochemical properties; electron affinity; proton affinity; neutron affinity; or any other physical or chemical property, including but limited to solubility, polarizability, melting point, boiling point, triple point, dipole moment, magnetic moment, size, shape, acidity, basicity, isoelectric point, diffusion coefficient, or sedimentary coefficient. Such molecular tag could be detected or identified via one or any combination of such properties.

In certain embodiments of the invention, the particles of the present invention may include mono-molecular layers. Such mono-molecular layers may be found at the tips or ends of the particle, or between segments. Examples of the use of monomolecular layers between segments are described in the section below entitled *ELECTRONIC DEVICES*.

The present invention is directed to freestanding nanobar codes and their uses. By "freestanding" it is meant that nanobar codes that are produced by some form of deposition or growth within a template have been released from the template. Such nanobar codes are typically freely dispensable in a liquid and not permanently associated with a stationary phase. Nanobar codes that are not produced by some form of deposition or growth within a template (e.g., self-assembled nanobar codes) may be considered freestanding even though they have not been released from a template. The term "free standing" does not imply that such nanoparticles must be in solution (although they may be) or that the nanobar codes can not be bound to, incorporated in, or a part of a macro structure. Indeed, certain embodiments of the invention, the nanoparticles may be dispersed in a solution, e.g., paint, or incorporated within a polymeric composition.

The particles of the present invention may be used for a variety of applications. There are two major classifications of uses: those embodiments where the segments of the particle have informational content, and those where the segments do not have informational content. In those embodiments where the segments have informational content, the best analogy is to macroscopic bar coding. Conventional bar coding provides for a strip of black lines whereby the distance between lines and thickness of the lines are used to "code" a significant amount of information. Because of the small size of the particles of the present invention, in certain embodiments it is possible to use the particles of the invention as molecular tags. Unique identifying tags that can be "read" can be attached to any material including to molecular entities in order to track molecular events.

Non-informational modes of the invention include embodiments where differential reactivities of the segments of the particles are utilized to provide nanoscale templates. Examples of differential reactivities can be seen when the particles are comprised of different metal segments. Gold binds thiol containing compounds, platinum-isocyanides, copper-dithiocarbamates, nickel-glyoximes. The precisely controlled dimensions of the particles of the present invention, coupled with the differential reactivity of the segments, allows for applications of the invention where precise nanometer separations are required. For example, using the nanoparticles of the present invention and the electroplating process as described generally below in FIG. 1, it is possible to create relatively precise segment lengths. Molecular interactions may be studied by separating species attached to the surface of the segments and varying the length of the segment between the differently functionalized segments, thereby precisely tuning the distance between the species. In still other embodiments, the particles of the present invention may be useful due to the physical properties achieved by the juxtaposition of segments. For example, chemical reactions that occur only at the surface of interfaces between two metals could be optimized by catalysis using particles of this invention.

The particles of the present invention may be prepared by a variety of processes. The preferred process for the manufacture of a particular particle can often be a function of the nature of the segments comprising the particle. In most embodiments of the invention, a template or mold is utilized into which the materials that constitute the various segments are introduced. Defined pore materials are the preferred templates for many of the preferred particles of the present invention. $Al_2O_3$ membranes containing consistently sized pores are among the preferred templates, while porous polycarbonate membranes, zeolites and block co-polymers may also be used. Methods for forming segments of particles include electrodeposition, chemical deposition, evaporation, chemical self assembly, solid phase manufacturing techniques and photolithography techniques. Chemical self assembly is a method of forming particles from preformed segments whereby the segments are derivitized and a chemical reaction between species on different segments create a juncture between segments. Chemically self-assembled nanoparticles have the unique ability of being controllably separated between segments by reversing the chemical bond formation process.

Figure 5:
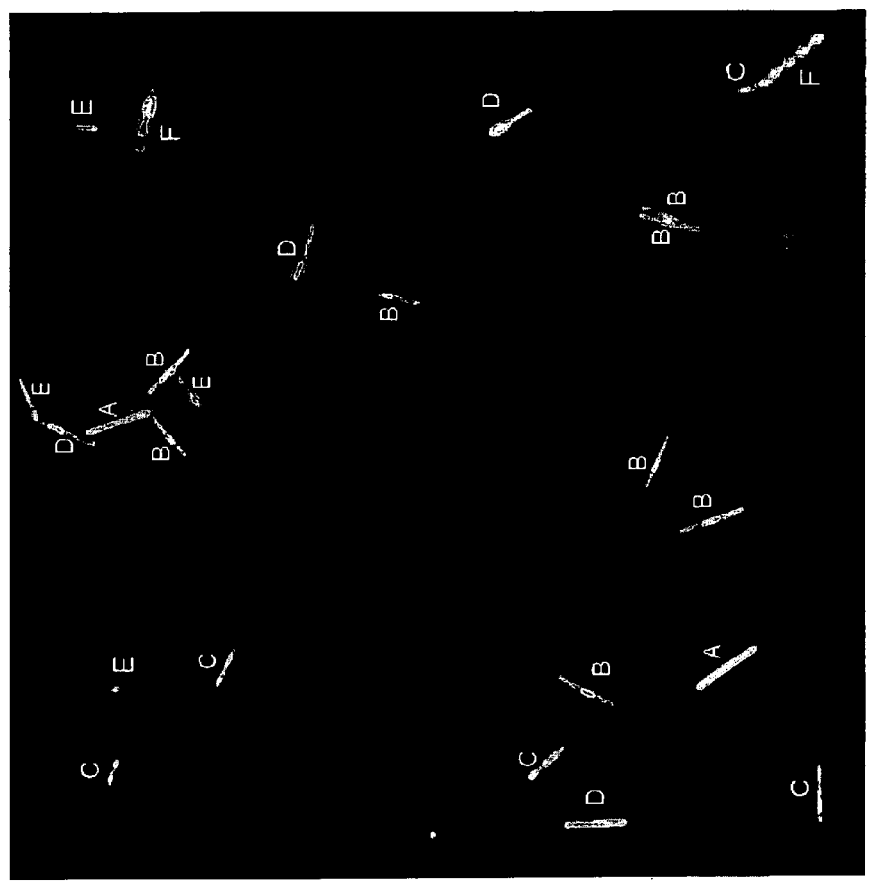
FIG. 5 is an image that shows an assembly of six types of nanobar codes. The figure diagramatically illustrates the six flavors of nanobar codes, A-F, and the image is labeled to show which of the nanobar codes in the image correspond to the various flavors or types of nanobarcode.
Figure 5:
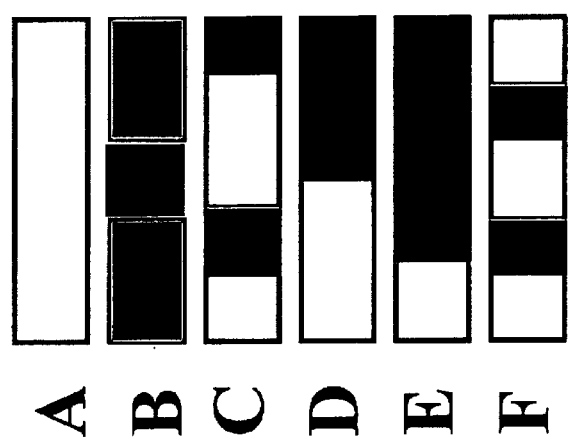

A key property of certain embodiments of the particles of the present invention is that when the nanorods are segmented, differences in the reflectivities of the component metals can be visualized by optical microscopy. Thus, in a segmented Au/Pt/Au rod of 200 nm in diameter and 4–5 microns in overall length, the segments are easily visualized in a conventional optical microscope, with the Au segments having a gold lustre, and the Pt segments having a more whitish, bright lustre. Another key property of the materials is that the length of the segments, when they are prepared by alternating electrochemical reduction of two or more metal ions, is controlled (and defined) completely by a) the composition of the solution and b) the number of Coulombs of charge that are passed in each step of an electrochemical reduction. Thus, the widths and the number of the segments can be varied at will. FIG. 5 shows an image of a collection of nanoparticles of the present invention comprised of six different types or flavors of nanoparticles. This image demonstrates the ability to differentiate between the different types of nanobar codes in a collection of nanobar codes.

Another key property of certain embodiments is that, like other metal nanoparticles, it is easy to derivatize or functionalize their surfaces, using a variety of different approaches. In this fashion, biomolecules can be attached to the surface via covalent or non-covalent means, in a manner that preserves full biological activity.

The ability to identify a nanobar code via its reflectivity and the ability to modify their surfaces with biomolecules allows the nanobar codes to be used as optical tags.

The nanobar code particles of the present invention can be used as tags in virtually any application where fluorescent tags or quantum dots are now used, or in conjunction with any assay or analytical procedure familiar to those skilled in the art. For example, a standard sandwich type immunoassay can be conducted wherein the nanobar code particle of the present invention serves as the stationary phase. The surface of the particle is functionalized to include an antibody to an analyte. When an analyte binds to said antibody a second fluroescently labeled antibody signals the presence of the analyte. The use of the nanobar code allows multiplexing by enabling the ability to conduct large numbers of assays at the same time. Positive signals can be identified and the nanobar code read to determine which analyte has been detected. The same general principle can be used with competitive assays as they are widely known to those skilled in the art.

Like macroscopic bar codes, which are based on difference in contrast of closely spaced lines of ink or other materials, in many embodiments the nanobar codes of the present invention are distinguished or identified based on different patterns of reflectivities of the various segments. What distinguishes nanobar codes from other types of optical tags, or indeed from any type of tag ever applied to a molecular system (including isotopic tags, radioactive tags, molecular tags for combinatorial beads, fluorescence-based tags, Raman-based tags, electrochemical tags, and other tags known to those of skill in the art,) is the essentially unlimited variability. With the ability to use 7 or more different metals, 20 or more different segments, and 4 or more different segment lengths, and with 3 or more different rod widths, there are essentially an infinite number of different nanobar codes that can be prepared. Even with just two types of metals and just 10 segments, with just one segment length, and with just one rod width, over a thousand different types (henceforth "flavors") of nanobar codes can be prepared.

Though the particles of the present invention are enormously useful even when prepared one batch at a time, methods to prepare hundreds, thousands, and even tens of thousands of different flavors of particles simultaneously are possible. The particles of the present invention can be read using existing instrumentation, e.g., chemical force microscopy, optical readers, etc. However, instrumentation and software specifically designed to identify nanobar codes are also within the scope of this invention.

Other distinguishing characteristics of nanobar codes is their stability. Thus in preferred embodiments, since the readout is based on differential reflectivity, they cannot be photobleached or photodegraded. Moreover, when composed, for example, of Pt and/or Au, two of the most durable and inert metals known, they can be heated, burned, frozen, etc., with no change in the relevant physical properties.

A unique characteristic of nanobar codes, is the ability to differentially modify their surfaces. Thus, considering Au/Pt nanobar codes, each metal may be selectively modified, providing two different chemistries to be placed in close proximity. In the case of nanobar codes, the ability to put different molecules on the Pt and Au stripes of a single particle has been demonstrated. The ability to rationally modify selected parts of a nanoparticle is without precedent.

It is possible to selectively modify Pt stripes with "Chemistry A" and Au stripes with "Chemistry B". This capability leads to the possibility that multiple sensors can be assembled orthogonally on the same particle, and read out independently from the same particle by the spatial pattern of fluorescence. For example, two separate sandwich immunoassays (using fluorescently-tagged secondary antibodies) could be carried out on a single nanoparticle having Au segments and Pt segments that have been derivitized with different antibodies, the fluorescence intensity from the Au stripes being proportional to one antigen concentration, and fluorescence intensity from the Pt stripes corresponding to the other. Note, also, that a different particle with a different segment pattern could harbor two completely different sensors: in each case, it is the bar sequence and spacing that identifies a particular chemistry. In addition, it is also possible to create colloidal rods containing three or more types of segments and with three or more orthogonal chemistries. The key point is that, according to this invention it is possible to truly carry out multiplexed assays on single particles (in addition to the intrinsic multiplexing allowed by bar coding).

Another feature of the nanobar codes of the present invention is the ability to identify them by conventional flow cytometry. Thus, light scattering can identify the overall length of a nanobar code flowing past a laser; more generally, scattering from metal nanoparticles is known to depend on particle size, particle shape, and particle composition.

Figure 2:
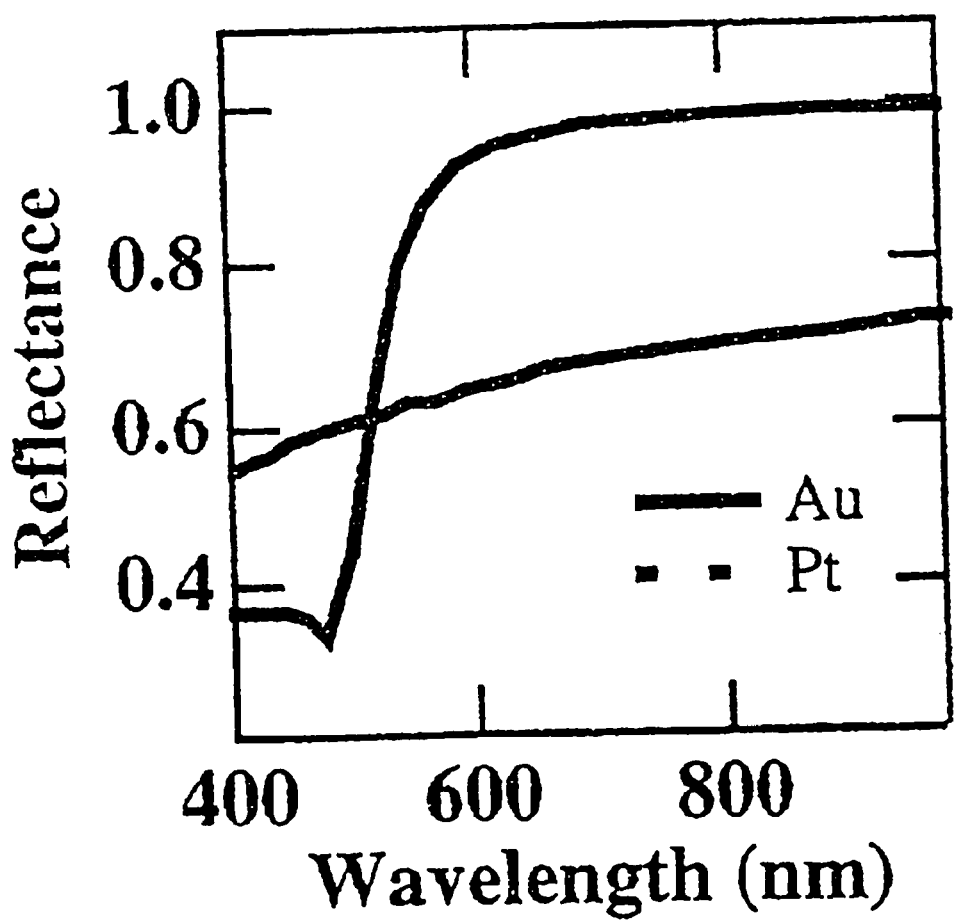
FIG. 2 shows a graph of reflectivity versus wavelength for bulk Pt and Au.

The wavelength dependence of metal reflectivity presents another interesting and powerful detection format for nanobar codes. For example, if one looks at the %reflectivity vs. wavelength plots of Au and Pt, there is a crossing point (FIG. 2). In other words, there is a wavelength at which the reflectivities of the metals are the same. This is referred to as a reflectivity isosbestic. At the reflectivity isosbestic, the reflectivity of a nanobar code is uniform, even though there is variation in composition along its length. Importantly, this reflectivity isosbestic can be perturbed by binding particles (e.g., metal or organic) to the nanobar code surface or by other means. Thus, molecular recognition or any other events that lead to binding (or debinding) of particles to the surface of a nanobar code can be used to detect that event by reflectivity. For example, consider 100 different flavors of nanobar codes, each associated with a different capture antibody in a solution that contains the hundred corresponding secondary antibodies, each tagged with a colloidal Ag nanoparticle. The particles are observed at the reflectivity isosbestic, and all appear uniform. Introduction of a solution containing one or more of the antigens will lead to formation of antibody-antigen-antibody complexes at certain nanobar codes. At these and only these nanobar codes, the metals' reflectivities will be perturbed (differentially), and there will no longer be an isosbestic, meaning that those nanobar codes can be identified by their segmented patterns. Reflectivity isosbestics, and perturbations thereof, thus allow rapid screening in complex, multiplexed assays, in that a "signal" (e.g., a discernable pattern) can be expected to occur only for a small subset of the nanobar code flavor population.

It is important to note that beyond simple identification using reflectivity isosbestics, the intensity of the differential reflectivity in the aforementioned example can be used for quantitation.

Figure 6B:
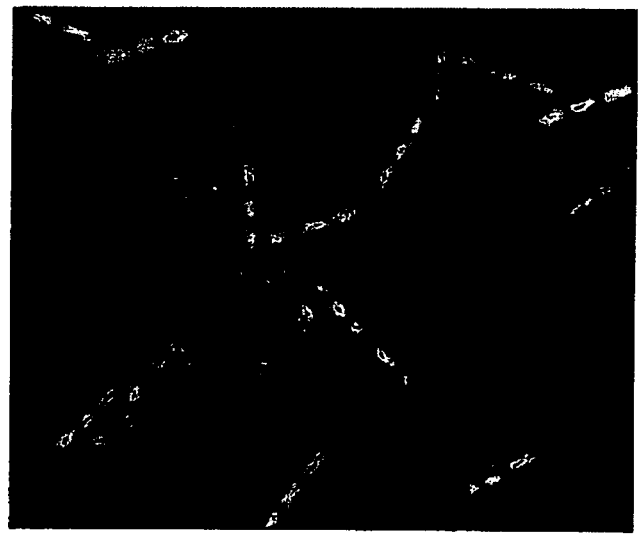
FIG. 6A is an image of a collection of Ag/Au nanorods at 400 nm and FIG. 6B is an image of the same collection at 600 nm.
Figure 6A:

FIG. 2 shows a plot of reflectivity vs. wavelength for bulk Pt and Au. Because of the finite-size effect, the plot would differ somewhat for nanoparticles, but the two relevant points are that (a) at most wavelengths, the reflectivity is different (thereby providing a contrast mechanism) and (b) at about 600 nm, they have the same reflectivity (a reflecting isosbestic). FIG. 6 shows images of gold and silver nanoparticles at 400 nm and 600 nm, demonstrating this principle. It is well-known how bulk reflectivity of the thin metal films in the visible region of the electromagnetic spectrum depends on morphology; this is especially so for noble metal surfaces, in which nanometer-scale roughness features can act as scattering sites for surface plasmons. This leads to greatly enhanced antigen sensitivity. Translating this concept to bar codes, the idea is that molecular recognition-induced binding of colloidal Au to the Au segments of a colloidal bar code will change the bulk reflectivity, and at a reflectivity isosbestic, will lead to reflectivity contrast. One could thus consider the colloidal metal nanoparticles to be contrast agents. This reflectivity contrast mechanism—which is essentially a solution analogue to surface plasmon resonance—has the potential to be exquisitely sensitive. Using commercial instrumentation, it has been shown that detection of one 40-nm diameter colloidal Au particle per 10 square microns is easily attainable. Because the surface area of the bar code is much less than 1 $\mu m^2$, it is anticipated that binding of a single particle to a single segment will be detectable; furthermore, methods to limit the colloidal coverage of a biomolecule of interest to one per particle are possible.

Another very significant aspect of the detection mechanism of this embodiment is that only those bar codes that bind colloidal Au will exhibit contrast, an enormous benefit in screening. Thus, one could have in solution 100 different types of bar codes, each derivatized with a different capture molecule and the appropriate colloidal Au-tagged recognition elements. Interrogated at the reflective isosbestic, the rods would all be featureless. Introduction of a solution with one unknown would cause just one type of bar code to light up, with the analyte identified by the code, and the analyte concentration defined by the integrated reflectivity change. Like the molecular beacon approach used to detect longer oligonucleotides in molecular biology by selective interruption of fluorescence quenching (see, e.g., Piatek et al., Nature Biochem. 16, 359–363 (1998)), this method singles out particles where chemical events have occurred, with the added advantage that the method is completely general, and can be applied to oligo-oligo, antibody-antigen, and ligand-receptor systems.

Thus, at least two different ways to do analyte quantitation are envisioned, one in which quantitation is made on the basis of the fluorescence intensity emanating from a particular nanobar code (which could derive from a molecular or particulate fluorescent tag), or from the intensity of the differential reflectivity. In both cases, reflectivity is also used to identify the nanobar code. It should be noted, however, that a variety of other schemes can be used both for analyte quantitation and nanobar code flavor identification. For analyte quantitation, these could include, but are not limited to, fluorescent tags, electrochemical tags, radioactive tags, mass tags (such as those used in mass spectrometry), other molecular tags (such as those used in combinatorial chemistry), or other particulate tags. Indeed, nanobar codes appear to be compatible with all known analyte detection mechanisms. Likewise, for nanobar code identification, a variety of detection mechanisms can be used, including but not limited to optical detection mechanisms (absorbance, fluorescence, Raman, hyperRaman, Rayleigh scattering, hyperRayleigh scattering, CARS, sum frequency generation, degenerate four wave mixing, forward light scattering, back scattering, or angular light scattering), scanning probe techniques (near field scanning optical microscopy, AFM, STM, chemical force or lateral force microscopy, and other variations), electron beam techniques (TEM, SEM, FE-SEM), electrical, mechanical, and magnetic detection mechanisms (including SQUID).

Although many embodiments are focused on antibody-based detection schemes, it should be recognized that these principles apply equally well to detection of oligonucleotides, cDNA, mRNA, proteins, ligands, small molecules, lipids, sugars, inorganic anions and cations, cells or cell components, organs, organ systems or even whole organisms. In other words, nanobarcoding can in principle be used to detect any and/or all species found in chemical or biological systems, as small as molecules and as large as organisms. Moreover, since nanobar codes are small enough to penetrate cells, and in principle can be made small enough to penetrate components of cells (e.g. mitochondria, nucleus, etc.), there is no limitation to their use in biological systems.

Moreover, it should be clear that while many embodiments of the invention are directed to quantitation, nanobarcoding, like its macroscopic counterpart, can be used for tracking, locating, or following matter in a non-quantitive fashion. Indeed, these particles can be used to label, detect, quantify, follow, track, locate, inventory, recognize, compare, identify, spot, make out, classify, see, categorize, label or discover matter, from sizes as small as individual molecules to as large as humans, cars, tanks, bridges, buildings, etc.

Moreover, it should be clear that many embodiments of the invention are directed to utility in biological systems, nanobarcoding is of equal utility in the aforementioned ways for non-biological systems, including but not limited to chemicals, molecules, materials, particles, paints, fasteners, tires, paper, documents, pills, and so on. When used as tag or label, the particles of the present invention can be associated in any way with the material it is labeling. The particular tag can be selected and identified so that it provides information regarding the material it is associated with. For example, a tag within a paint may encode the date of manufacture, the chemicals used in the paint mix, the name of the manufacturer, photodynamic characteristics of the paint or any number of other pieces of information. By saying that the nanobar code encodes information does not imply that you can read the information off of the particle. It, in most embodiments, will indicate a specific type of nanobar code, and reference would then be made to records concerning that type of nanobar code.

In one embodiment of the invention the nanoparticles are not comprised of segments, but are differentiable based on their size, shape or composition. In this embodiment, each particle in an assembly or collection of particles has at least one dimension that is less than 1 μm. In preferred embodiments, the particles have one dimension less than 500 nm, and more preferably less than 200 nm.

Such an assembly of particles, which can be made up of any material, is comprised of at least 2, preferably at least 3, and most preferably at least 5 types of particles, wherein each type of particle is differentiable from each other type of particle. In the preferred embodiment, since the types of particles may be comprised of a single material and since different types of particles may be comprised of the same material as other types of particles in the assembly, differentiation between the types is based on the size or shape of the particle types. For example, an assembly of particles of the present invention may be comprised of 5 different types of gold rod-shaped nanoparticles. Although, each type of rod-shaped particle has a width or diameter of less than 1 μm, the different types of particles are differentiable based on their length. In another example, 7 types of spherical silver particles make up an assembly. The different types of particles are differentiable based on their relative size. In yet another example, 8 types of rod-shaped particles, all composed of the same polymeric material, make up an assembly; although each type of rod-shaped particles have the same length, but they are differentiable based on their diameter and/or cross-sectional shape.

The nanoparticles of this embodiment of the present invention may be functionalized as described above, and used in the same types of applications as the segmented nanobar code particles. In an assembly of particles, according to this embodiment, the particle types may be, but are not necessarily composed of the same material.

A further example of an assembly of nanoparticles that fall within the scope of this embodiment of the invention is an assembly of particles, each type of which may have the same size and shape (with at least one dimension less than 1 μm) where the particle types are differentiable based on their composition. For example, an assembly of particles of the present invention may be comprised of 5 different rod-shaped nanoparticles of the same size and shape. In this example, the different types of particles are differentiable based on the material from which they were made. Thus, one type of nanorod is made from gold, another from platinum, another from nickel, another from silver, and the remaining type from copper. Alternatively, each particle type may contain a different amount of a dye material, or a different percentage of magnetizable metal. In each case, a given particle type would be differentiable from the other particle types in the assembly or collection.

Of course, this embodiment of the invention includes assemblies or collections in which combinations of size, shape and composition are varied. The critical aspect of the assembly of particles of this embodiment is the fact that all particle types have at least one dimension less than 1 μm and that the particle types are differentiable, by any means, from the other particle types in the assembly. In this embodiment, the different types of particles may be functionalized and the differentiable characteristics of the type of particles encodes the nature of the functionalization. By encoding the nature of the functional unit, it is meant that the specific identifiable features of the nanoparticle can be attached selectively to a known functional unit, so that a key or log can be maintained wherein once the specific particle type has been identified, the nature of the associated functional unit is known.

Preparation of Metallic Segmented Particles

The preferred synthetic protocol used to prepare metallic nanobar codes according to the embodiments of the present invention is based on the work of Al-Mawlawi et al. (Al-Mawlawi, D.; Liu, C. Z.; Moskovits, M. *J Mater. Res.* 1994, 2, 1014; Martin, C. R. *Chem. Mater.* 1996, 8 1739) on template-directed electrochemical synthesis. In this approach, metals are deposited electrochemically inside a porous membrane. The synthetic method of the present invention differs from previous work in three respects. First, the electroplating is done in an ultrasonication bath. Second, the temperature is controlled using a recirculating temperature bath. These first two modifications increase the reproducibility and monodispersity of rod samples by facilitating the mass transport of ions and gases through the pores of the membrane. Third, rods with multiple stripes are prepared by sequential electrochemical reduction of metal ions (e.g., $Pt^{2+}$, $Au^+$) with in the pores of the membranes. Because the length of the segments can be adjusted by controlling the amount of current passed in each electroplating step, the rod resembles a "bar code" on the nanometer scale, with each segment length (and identity) programmable in advance. While the width of the rods and the segment lengths are generally of nanometer dimensions, the overall length is generally such that it can be visualized directly in an optical microscope, exploiting the differential reflectivity of the metal components.

There are many parameters in the nanorod synthesis that are tunable, such that it is theoretically possible to generate many millions of different patterns, uniquely identifiable by using conventional optical microscopy. The most important characteristic that can be changed is the composition of the striped rods. The simplest form of a nanoparticle is one with only one segment. To this end, several different types of these solid bar codes have been prepared. By simply using only one plating solution during the preparation, a solid nanoparticle is produced.

Figure 3:
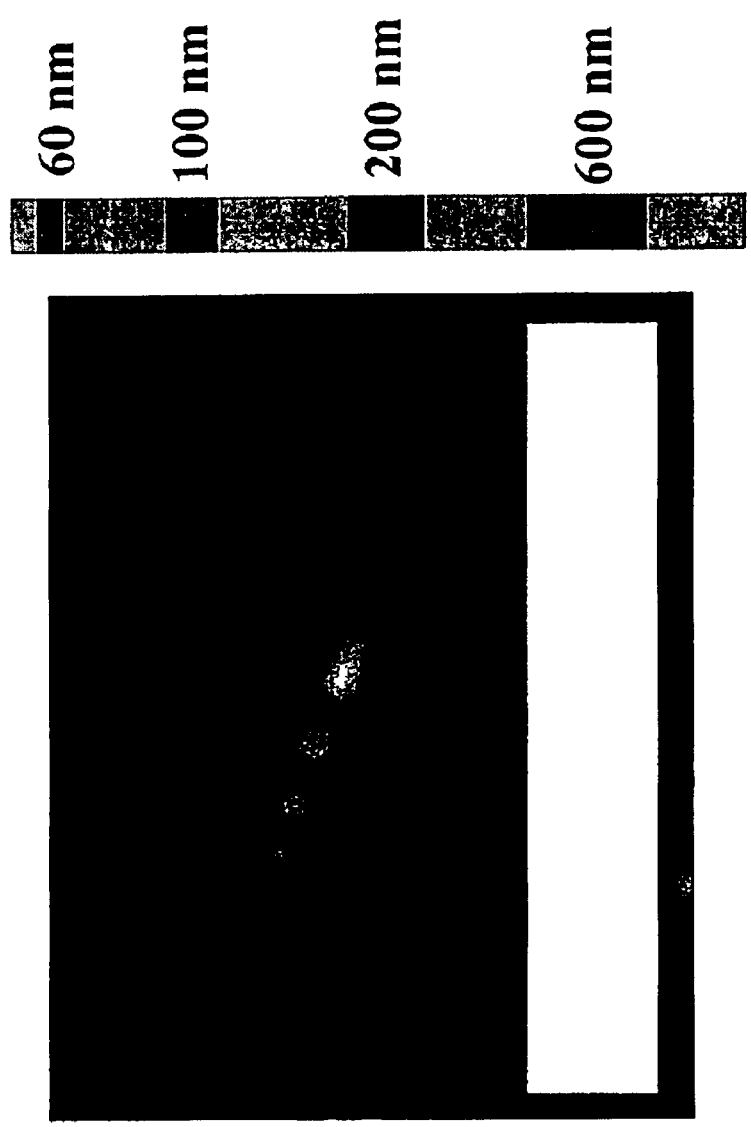
FIG. 3 is an image taken from an optical microscope in reflected light mode of a 9-striped bar code (Au/Ag/Au/Ag/Au/Ag/Au/Ag/Au) of the present invention.

To generate two-segment nanobar codes, two metals (e.g., Au, Ag, Pd, Cu, etc.) can be electroplated sequentially or simultaneously to form alloys. Nanobar codes can also be generated using 3 different metals. Synthesis of a Au/Pt/Au rod may be accomplished with 1 C of Au, 8 C Pt, and 1 C of Au. The nominal dimensions of the segments are 1 μm of Au, 3 μm of Pt, 1 μm of Au. The 5-segment nanobar codes, Ag/Au/Ag/Au/Ag, were generated by sequentially plating and optionally rinsing the appropriate metal. In some embodiments it is possible to include all metals in solution but control deposition by varying the charge potential current A nine-segment nanobar code, Au/Ag/Au/Ag/Au/Ag/Au/Ag/Au seen in FIG. 3 has also been prepared. The number of segments can be altered to desired specifications.

The next controllable factor is diameter (sometimes referred to herein as width) of the individual rods. Many of the nanobar codes described were synthesized using membranes with a pore diameter of 250 nm. By altering the pore diameter, rods of differing diameter can be made. Au rods have been synthesized in a membrane that has 10 nm diameter pores and 40 nm pores.

The ends of the rods typically have rounded ends or flat ends. A TEM image of an Au rod that was made by reversing the current flow (from reduction at −0.55 $mA/cm^2$ to oxidation at +0.55 $mA/cm^2$) and removing some of the gold from the tip of the rod generated a spike extending from the tip of the rod. Additionally, branched ends can be generated. This can be typically controlled by controlling the amount of metal that is plated into the membrane. The edges of the membrane pores have a tendency to be branched which lead to this type of structure.

An additional way to alter the ends of the rods is to control the rate of deposition. Gold rods (2 C total, 3 μm) were plated at a current density of 0.55 $mA/cm^2$. Then the current density was reduced to 0.055 $mA/cm^2$ and 0.1 C of Au was plated. The last segment of gold deposits is a hollow tube along the walls of the membrane.

In order to produce many thousands of flavors of nanorods, in practical quantities, and to attach molecules to most or all, novel combinatorial synthesis techniques are necessary. Several synthesis embodiments are included within the scope of the invention. Each approach has advantages and disadvantages depending on the specific application and the required number of types and total number of nanorods needed for the application.

Three of the embodiments are based on existing procedures using defined-pore membranes. (i) The first technique generates hundreds to perhaps a few thousand types of nanorods, by lithographically patterning the backside silver that is deposited on the membrane into isolated islands, each island forming an individually addressable electrical contact. By way of example, each island would have enough surface area to contain between $10^6$ and $10^8$ individual rods, all of the same type. (Note that since the membrane thickness, and therefore pore length, is much greater than the nanorod length, multiple nanorods can be synthesized in each pore. Each nanorod may be separated from others in the same pore by a silver plug that would later be dissolved. This could increase the total yield by 10x.) The membrane is then placed, with careful registration, onto a "bed-of-nails" apparatus, with individual spring-loaded pins contacting each electrode on the membrane. Computer-controlled circuitry attached to the bed-of-nails is able to individually turn on or off each electrode. During the electroplating process, each island would be plated with unique combinations of metal types and thicknesses. In this manner, each island would produce rods of different lengths, different numbers of stripes, and different material combinations, allowing ultimate design flexibility. (ii) The first approach will be limited in the number of types of rods that can be synthesized by the reliability and packing density of the bed-of-nails apparatus. To avoid this limitation, the bed-of-nails apparatus can be replaced by a liquid metal contact. To prevent the liquid bath from simultaneously contacting every electrode, the backside of the membrane may be patterned with a nonconductive coating. To individually address electrodes during synthesis, the pattern would be removed and replaced between electroplating steps. This approach will enable a much higher density of isolated islands, and therefore more types of rods to be synthesized. With island spacing of 100 microns, which would be trivial to achieve using lithographical patterning, up to $10^5$ types of rods could be synthesized. Since the total number of pores in each membrane is a constant there will be proportionally fewer rods of each type. (iii) The first two approaches use commercially available aluminum oxide membrane filters, which have pore size and density that are suitable for nanorod synthesis. However, the membrane thickness is typically greater than that required, which can cause variability in rod and stripe lengths due to non-uniform mass transport into the pores during electroplating. Also, the largest pores available in these membranes (and thus nanorod widths) are 250 mm, and it would be desirable for some applications to have rod widths of 1 micron or more (this could also be used for embodiment with widths of less than 1 μm). To address these issues, pore matrices may be constructed using photolithography techniques, which will give ultimate control over the pore dimensions and lengths, and increase the design flexibility and quality of the resulting nanorods. According to this embodiment a positive photo resist coated wafer is exposed to an interference pattern of light, using a technique similar to that used for lithography-generated diffraction gratings. Two exposures at right angles and subsequent development yields an array of vertical holes in the photo-resist. Electroplating of metal into the holes and removal of the photo-resist yields a new type of template for template-directed synthesis. The shape and diameter of the nanorods could be controlled by adjusting the light source and the resultant standing wave pattern. An advantage to this technique is that the template thickness, which is the same as pore length, can be tailored to the length of the rods, which improves uniformity of electroplating across the membrane. With this technique, $10^{10}$ to $10^{12}$ types of nanorods can be constructed on a single substrate. The two approaches described above can be utilized to synthesize many types of nanobar code from a single wafer. (iv) A further approach uses the customized lithographically-defined pores from above, and achieves the ultimate in design flexibility by using novel light-directed electroplating. The template pores are constructed just as in the third approach, but on top of a photosensitive semiconductor wafer. The pore-side of the wafer is immersed in electroplating reagent, and the other side is illuminated with patterns of light. Light exposure is used to generate photocurrent in the wafer, and switch the plating current on or off for each conductive zone within the wafer. A computer-controlled spatial light modulator selectively illuminates different zones at different times, so that each zone will be subjected to a different computer-controlled plating recipe. Depending on the resolution of the optical system that exposes the wafer, this could result in $10^4$ to $10^6$ separate flavors of nanorods synthesized on a single wafer. With $10^{12}$ total pores per wafer, $10^6$ to $10^8$ nanorods of each flavor could be synthesized.

The particles of the present invention may also be prepared in large scale by automating the basic electroplating process that is described in Example 1. For example, an apparatus containing a series of membranes and separate electrodes can be used to make a large number of different flavors of nanoparticles in an efficient computer controlled manner.

Independent of the synthetic approach used, a final critical step is required to separate each unique type of nanorod and release all the nanorods into solution, for surface preparation or denaturation. Each of the above synthesis approaches can utilize the same process for nanorod separation and release. There are two primary techniques. (i) Following synthesis, whether on membrane or planar substrate, die separation techniques from the semiconductor industry can be utilized. The substrate will be mated to a flexible adhesive material. A dicing saw cuts through the substrate, leaving the adhesive intact. The adhesive is then uniformly stretched to provide physical separation between each island, each of which is then picked up automatically by robot and placed into a separate microwell. An automated fluidics station is used to introduce the necessary etching solutions to release each rod into solution. (ii) An alternative embodiment is a matching microwell substrate that contains wells in the same pattern as the individual islands in the membrane, and a matching array of channels through which flow etching solutions. The membrane or wafer can be sandwiched between the microwell substrate and the channel array. Etching fluid is then introduced into the channels which dissolves the Ag backing and carries the nanorods into the corresponding well. Other means for removing the particles from the membrane are also possible, including laser ablation, controlled acid or base ablation, and so on.

Uneven plating across the membrane or deposition on the planar substrate will result in variations in stripe length and therefore impose limitations on minimum stripe length. At some point, this limits the number of stripes, and thus the maximum number of possible types, for a given nanorod length.

The membrane-based template-directed synthesis techniques are preferred because they are capable of making a very large number of very small nanorods. The electroplating conditions can be adequately controlled to produce many types of nanorod bar codes. For applications such as multiplexed immunoassays, where tens to many hundreds of types are required, known techniques are adequate and can simply be scaled up to provide the necessary number. For applications such as proteomic signatures, where many thousands of types are required, higher throughput synthesis techniques and the ability to uniquely identify each of thousands of different bar codes are required.

Algorithms and techniques from the telecommunications, disk drive, and bar code industries can be utilized to determine the optimum nanorod designs to yield the most "information" in a given length of nanorod. The fundamental challenge of encoding information in a noisy communications channel, and detecting the information with a minimum of errors, is well known. Solutions that have been applied to these problems will be relevant to the design, synthesis, and detection of nanorod bar codes.

Nanobar Code Detection and Identification

The ability to make complex bar codes is of no consequence without an effective method for reading the bar codes. Fortunately, in the case of metallic bar codes of approximately 100 nm or more in width and about 2 microns to 15 microns in length, differences in metal segment reflectivities can be visualized using conventional light microscopy. Thus, is possible to distinguish (and quantify) the number of rods by visual inspection; such a task could be automated. It is also possible to distinguish segments of different lengths within individual bar codes. Images have been obtained of a 9-striped bar code (Au/Ag/Au/Ag/Au/Ag/Au/Ag/Au) in which the four Ag segments were grown to different lengths. See FIG. 3. The image was obtained using an optical microscope in reflected light mode, using a 400±40 nm bandpass filter to improve resolution and enhance image contrast.

The image is interesting in several respects. First, it is clear that four distinct bright regions can be seen (which correspond to Ag segments). In this image, the apparent lengths (by microscopy) do not correspond to the estimated lengths. For example, the smallest bright segment does not appear to be one-tenth the length of the longest segment. This may be due to a non-linear current vs. length relationship, but more likely reflects physical limitations of the optics. The image was obtained with reflected light bright field microscopy. In this mode, the diffraction-limited optics give a theoretical resolution of about 2NA where NA=numerical aperture (in the system used to obtain these images, the resolution is about 400 nm/2(1.4)=143 nm). Thus, it is possible to distinguish two features as close together as 143 nm (Rayleigh criterion). Points closer together than this will appear as a single feature. However, note that an Ag stripe shorter than 143 nm is still visible under the microscope, since the Au sections separating it are longer than this distance. Thus, for a 2.5 micron bar code, one can easily imagine 12 stripes of 200 nm each, all of which are optically distinguishable. Alternately, it should be possible to create and "read" bar code rods of 2 micron having 10 stripes, with five segments of 150 nm and five segments of 50 nm.

Simultaneous bar code detection by reflectivity and analyte quantitation by fluorescence is possible. An example is shown in FIG. 4. Panel C shows a reflectivity image obtained at 400 nm that is used to identify each type of nanorod. In this case, the image shows a mixture of striped nanorods. Panel A, imaged at the wavelength of FITC emission, contains bright images of the first type of nanobar codes, and barely detectable ghosts of the second type of nanobar codes, which are easily subtracted digitally. In Panel B, imaged at the wavelength of Texas Red, the second type of nanobar codes show brightly, while the first type of nanobar codes are extremely dim.

The ability to read fluorescence and ID nanobar codes simultaneously comprise a powerful set of tools for multiplexed assays. However, there are a large number of bioanalyses carried out by means other than fluorescence. Prominent among these is mass spectrometry, rapidly becoming the tool of choice for detailed identification and analysis of polypeptides and proteins. There are two widely-used methods for biomolecular sample introduction in mass spectrometry: electrospray and matrix-assisted laser desorption/ionization (MALDI). In MALDI, the analyte of interest is embedded into a solid ultraviolet-absorbing organic matrix that vaporizes upon pulsed-laser irradiation, carrying with it the analyte. (See, e.g., Karas et al., Anal. Chem. 60, 2299–2301 (1988)). During this process the energy absorbed by the matrix is transferred to the analyte that is ionized. The gas phase analyte ion is then sent to the Time-Of-Flight (TOF) mass analyzer. MALDI-TOF is currently successfully utilized for the analysis of proteins, polypeptides and other macromolecules. Even though the introduction of an organic matrix to transfer energy to the analyte has advanced tremendously the field of desorption mass spectrometry, MALDI-TOF still has some limits. For instance, the detection of small molecules is not practical because of the presence of background ions from the matrix. Also, MALDI experiments are inherently sensitive to matrix choice: matrix type as well as matrix amounts must often be tailored to the nature of the analyte (a severe limitation to the analysis of complex mixtures).

Recently, Sunner et al. have introduced the term SALDI for Surface-Assisted Laser Desorption/Ionization (Sunner et al., Anal. Chem. 67, 4335 (1995)). This technique is matrix free, allows analysis of small organic molecules and yields performances similar to MALDI. Noble metal nanoparticles are a vastly superior choice for laser-based ionization, for two reasons. (i) Colloidal noble metal nanoparticles exhibit very large extinction coefficients in the visible and near IR. This contrasts with organic matrices. (ii) Irradiation of Au nanoparticles is known to lead to dramatic enhancements in electric field strength at the particle surface: this is the basis of surface-enhanced Raman scattering. This leads to increased ionization efficiencies. Moreover, combined with nanobar code technology, SALDI-MS becomes a powerful molecular fingerprinting tool.

Conventional light microscopy has been used to image the nanorods, and should allow for automated "decoding" of the bar code signature. Additionally, fluorescence microscopy has been used to quantify the level of binding of a biomolecule to the rod. The detection and readout can also be accomplished with custom instrument designs and sophisticated image analysis software that are capable of detecting and reading the code of each nanobar code, and quantifying the fluorescence from molecules bound to the nanorod.

Additionally, this detection system allows for highly focused laser excitation of the appropriate wavelength to enable laser-induced desorption of non-covalently bound molecules from the surface of each individual nanorod.

A system meeting these requirements can be made for imaging nanorods randomly dispersed on a glass surface. Using a 63×(NA=0.8) microscope objective mated to a 4k×4k pixel CCD camera, the field-of view of the camera is about $9 \times 10^4$ $\mu m^2$ (300 microns on edge). Each field of view can hold about 600 nanorods (1% coverage) with reasonably low probability of physical overlap. Conservatively assuming that it is desirable to detect and average the fluorescence or MS signal from about 10 rods of each type, a 1000-flavor measurement needs to identify and measure a total of 10,000 nanorods. With 600 particles per field of view, about 170 image frames covering a total area of about 20 $mm_2$ are required. For a high-speed camera, each frame read takes about 2 seconds, for a total imaging time of less than 10 minutes. Note that the surface area required is about the same as one well of a 96-well microplate, and that the total throughput is 1000 assays in 10 minutes, or about 1.7 seconds per assay.

Image analysis software may be used that is capable, in real time, of locating, decoding the stripe pattern, and quantifying fluorescence from each nanorod in the field of view. To save measurement time, the system may use two CCD cameras, one to capture reflected light to decode the stripe pattern, and the other to simultaneously quantify the fluorescence signal from each nanorod.

This imaging system is not only capable of detecting the stripe pattern but also is capable of simultaneously measuring fluorescence emission from each nanorod. In addition, it can be used to direct a highly focused laser spot, with the spot size matched to the largest dimension of the nanorod, at each individual nanorod. Beam steering optics can be used to sequentially illuminate and desorb proteins and and/or molecules from each nanorod, which will then be accelerated into a time-of-flight mass spectrometer. Individual nanorods can be chosen for mass spectrometric analysis based on the fluorescence signal detected, thus minimizing measurement time by analyzing only those rods with significant binding.

As discussed above, though the preferred embodiment involves reflectivity as the mechanism for particle identification and fluorescence as the sensor readout, reflectivity changes themselves could also be used, with a potentially large payoff, for sensing. The two relevant points illustrated by Pt and Au reflectivities, are that (a) at most wavelengths, the reflectivity is different (thereby providing a contrast mechanism) and (b) at about 600 nm, they have the same reflectivity (a reflectivity isosbestic). At 450 nm, the Pt stripes will appear brighter (more reflective) than Au, and that at 600 nm, the opposite is true. At an intermediate wavelength, there is a reflectivity isosbestic, where no contrast would be observed.

It is well-known how bulk reflectivity of thin metal films in the visible region of the EM spectrum depends on morphology; this is especially so for noble metal surfaces, in which nanometer-scale roughness features can act as scattering sites for surface plasmons. Briefly, antigen-directed binding of secondary antibodies tagged with small, spherical colloidal Au nanoparticles to thin Au films derivatized with capture antibodies leads to enormously amplified changes in the Au film reflectivity. This leads to greatly enhanced antigen sensitivity. Translating this concept to bar codes, the idea is that molecular recognition-induced binding of colloidal Au to the Au segments of a colloidal bar code changes the bulk reflectivity, and at a reflectivity isosbestic, leads to reflectivity contrast. One could thus consider the colloidal metal nanoparticles to be contrast agents. This reflectivity contrast mechanism, which is essentially a solution analogue to surface plasmon resonance, can be exquisitely sensitive. Using commercial instrumentation, it has been shown that detection of one 40-nm diameter colloidal Au particle per 10 square microns is easily attainable. Because the surface area of the bar code is much less than 1 $\mu m^2$, the binding of a single particle to a single segment will be detectable; furthermore, methods to limit the colloidal coverage of a biomolecule of interest to one per particle are possible.

The nanobar codes of the present invention have an almost limitless number of applications in the biosciences. Included among there are use in genomics, proteomics functional proteomics, metabolic profiling, small molecular analysis, combinatorial bead identification and phenotyping. There are also non-bioanalytical uses such as for traditional bar coding type applications and nano diodes. Several of these applications are described in detail below.

Genomics Applications

The nanobar code technology of the present invention is useful in at least one embodiment to: (i) monitor gene expression on, for example, 100 samples simultaneously; (ii) carry out genomic analyses on self-referencing particles; and (iii) to carry out single nucleotide polymorphism (SNP) analysis on 10,000 particles simultaneously in solution.

Practitioners of genomics aim to globally monitor gene expression and/or detect genetic polymorphisms within an organism. In humans, such a tool can be used both in diagnostic and prognostic medicine, explaining in part the enormous market capitalization of companies involved in gene chip production. However, even years after first commercial demonstration of gene chips, there are still some fundamental problems with the technology that have to be solved. Most prominent among these is the inability to compare large numbers of samples simultaneously, whether for the purpose of monitoring gene expression in various parts of a plant, or more importantly, for screening large numbers of patients. The very high level of multiplexing offered by nanobar coding alleviates these problems, making high-throughput, low cost genomics applications a reality.

In cDNA array-based analysis of gene expression as practiced today, mixtures of two cDNAs (each tagged with a different color of fluorescent dye) are applied to a surface containing a number of different cDNA spots; after hybridization, analysis of the intensity ratio of the two colors allows determination of upregulated, downregulated and unaffected genes. In theory, this could be carried out with mixtures of up to four samples of cDNA, using each of the four dyes used in DNA sequencing, for example. Such an experiment would allow gene expression to be monitored in different parts of an organism, for example (i.e. the roots, stem, leaves, and flower of a crop), or at different times after therapeutic intervention. In practice, this has not been demonstrated on a commercial scale: evidently, there are enough problems using just two colors that the prospect of using more is presently not viable. Moreover, it will simply not be possible to do large scale multiplexing (i.e. mixtures of tens to hundreds of samples of DNA) using current technology. In contrast, such an experiment will be very straightforward using bar coding, allowing rapid screening of large populations to be carried out, which would have significant consequences for early diagnosis of disease.

A surface comprising 50–100 spots of double-stranded (ds) cDNAs, focusing on a subset of genes of interest, such as those known to be relevant to a particular disease, can easily be prepared. Gene clusters very similar to these are now commercially available on membrane and/or glass supports. (Note that the white background of membranes could provide excellent contrast for nanobar code identification). Each spot is approximately 400 microns×400 microns in size. When each of 100 samples of isolated mRNA are reverse-transcribed to cDNA, a unique oligonucleotide tag (15 bases) will be appended to each poly-T primer; thus, all the cDNAs from each sample will have the same (unique) tag. In an example of the invention, fifty of the samples will come from a blood bank, and fifty will come from patients exhibiting early- or chronic-stage disease. The 100 samples of labeled cDNAs are be mixed and hybridized to the surface (after the ds cDNA on the surface is denatured) using standard protocols. If the level of mRNA expression were identical in each sample, then equal numbers of cDNA from each sample will bind to the surface. Using a coverage of $10^{12}$ cDNAs/cm$^2$, and only a 1% efficiency of hybridization (an underestimate), that corresponds to $1.6 \times 10^5$ of each unique cDNA on each spot ($1.6 \times 10^7$ total cDNA molecules). Samples with relatively greater or lower levels of expression are determined to exhibit increased or decreased numbers of molecules bound, respectively.

Quantitation of relative amounts of binding will come by developing this surface with a mixture of 100 flavors of nanobar codes, each tagged with a unique oligo complementary to that used to tag the samples of cDNA. It has been shown that because of roughness on the 5–10 nanometer scale along the lengths of the bars, hybridization proceeds more efficiently if oligos are spaced away from the nanobar code surface. Thus, the complementary tags will be affixed to the particles using a 45-mer, comprising 30 bases of a randomized DNA and the 15-base oligo. One of the well known methods are used to affix the 45-mer to the surface: one involves use of thiol-labeled DNA, and another uses standard EDC coupling to amine-terminated DNA. For the thiol labeled material, note that addition of the 45-mer to a particle pre-derivatized with mecaptohexanol increases the tendency of the DNA to bind normal to the surface (and thereby increase hybridization efficiency).

Note that the dynamic range of the measurement is reduced by the size of the nanobar codes relative to the size of the spots: a 0.1×1 micron bar code will cover 1000 cDNA molecules, meaning there will only be $1.6 \times 10^4$ bar codes on each spot, or only 160 of each flavor if there are no differences in expression, if the spot is 200×200 microns. If this relatively low dynamic range (i.e. 2 decades) is not sufficient, the number of samples can be reduced to fifty, and the spot size tripled, to give a 3-decade dynamic range. This does not require tripling of the required material. Related work has shown that a single linkage is sufficient to hold the attached species together.

This type of very high level multiplexing (i.e. multiple tags on multiple spots) cannot be carried out using any other current technology. With spherical particles, one can get different flavors, but the particles are so large compared to nanobar codes that only a few of each type could bind to a surface. One could put 100 different cDNAs onto such particles (i.e. one type on each), effectively allowing the array to be replaced with beads, but then one is constrained to 3–4 types of fluorescent tags. Alternatively, one could consider quantum dots, which are much smaller than bar codes, allowing more particles to bind to each spot, but there is no prospect in the near future of preparation of 100 different flavors: with a fluorescence half-width of 25 nm, a set of particles with emission maxima spaced evenly from 500 nm to 3 microns would be required. Nanobar codes offer the unique balance of small size and high readout tenability to enable this application.

The ability to place two different chemistries on the same Au/Pt nanobar code may also be used in this embodiment of the invention. This leads to two opportunities, self-referencing nanobar codes and dual-assay nanobar codes. Both opportunities stem from the fact that since it is possible to control which sets of stripes are within a single nanobar code, it is possible to control the position(s) on the particle from which fluorescence is observed. If, for example, a capture antibody is placed solely on the Au stripes and a sandwich immunoassay is carried out using a fluorescently-tagged secondary antibody, there should be no fluorescence emanating from the Pt stripes: the Pt stripes are acting as an internal standard. Thus, any fluorescence coming from the Pt must be ascribed to non-specific binding, and can be digitally subtracted. This principle can be demonstrated using matched and mismatched capture oligonucleotides on the different metals. This becomes a self-referencing nanoparticle.

Another key application that exploits differential stripe modification is for elimination of false positives in bioanalysis. For example, only 25% of the blood samples labeled positive for hepatitis C are actually positively contaminated. Accordingly, the FDA is now considering Nucleic Acid Testing of blood as a more accurate method. Ideally, a positive signal from both antibody- and nucleic acid-based tests would be required for unambiguous identification, especially when the consequences of a false positive are life-threatening. To that end, government agencies are actively pursuing complementary techniques for identification of biological warfare agents. The simultaneous detection of antigens and nucleic acids for anthrax, can also be accomplished using particles that are derivatized with antibodies on one set of stripes and oligos on the other (both the oligos and antibodies are available from Tetracore LLC, Rockville, Md.). The DNA assay will be carried out in "sandwich" mode. Only when the entire nanobar code surface emits light (i.e. both analytes are present) will a positive ID be made. In principle, this can be done with multiple suspected warfare agents, with the appropriate reagents immobilized on different flavors of nanobar codes simultaneously.

Other embodiments for utilizing the nanoparticles of the present invention become available with very large numbers of bar codes. For example, with 1,000–10,000 flavors of bar codes, enough nanobar code diversity is available to carry out complete genotypic analyses in solution, including single nucleotide polymorphism (SNP) mapping, without the complication (and expense) of gene chips or immobilized DNA. In this embodiment each flavor of nanobar code is an exact replacement for a spatial position on a gene array. Moreover, the experiment is carried out identically, except that the oligonucleotides will be attached chemically (i.e., by covalent adsorption of thiols, as described above) instead of by photolithography-driven reactions.

It is instructive to compare the amount of surface areas in arrays and nanobar codes (0.2×3 microns) for these experiments. A circular spot of 50 microns in diameter corresponds to an area of 2000 sq. microns. Carrying out synthesis on a 3" diameter membrane, and preparing 1536 nanobar codes/ membrane, with only one nanobar code per pore, and a pore density of 30% of the total membrane area, each synthesis will produce just over 28 million nanobar codes. Each 0.2 micron×5 micron bar code has an area of 3 sq. microns. Assume the efficiency of fluorophore detection on an immobilized nanobar code is the same as a similarly-sized spot on a planar array. Assume conservatively that only ⅓ of the fluorophores on an immobilized nanobar code can be detected (assume other ⅔ are on the bottom or the sides), the effective detection area per particle area is 1 sq. micron, so that the total available surface area (for each flavor of particle) is 28 million sq. microns, compared to 2,000 sq. microns for a gene chip. All other things being equal, each synthesis of nanobar codes produces enough of each flavor for the equivalent of 14,000 gene array experiments. (Note that you would do seven different syntheses of 1536 nanobar codes to get 10,000 different flavors, as typically is available in a genotyping experiment.)

Analysis of Small Molecules

A further embodiment of the nanoparticles of the present invention is combinatorial self-assembled monolayer chemistry on nanobar codes, to demonstrate acquisition of a SALDI-TOF spectrum of a molecule adsorbed to a SAM-coated nanobar code, and to demonstrate combinatorial separation/SALDI analysis on complex biological fluid.

Life scientists are increasingly interested in establishing complete profiles of proteins and peptides from patient samples, providing impetus for creation of the field of proteomics. Implicit in such efforts is the notion that changes in protein expression among samples from a diseased cohort may comprise a biomarker (or at least a component of a biomarker) for that disease. The complete profile of small molecules would be at least as interesting: after all, two of the most important biomarkers known to date are cholesterol and simple blood sugars, both exhibiting molecular weights considerably less than 1000. Unfortunately, beyond efforts at sequential separations (i.e. LC-CE or CE-CE) which have intrinsic theoretical limitations, there appear to be no rational approaches to 2-D small molecule separation.

In this embodiment of the present invention, it is possible to conduct compound separations on the surface of nanoparticles. The principle of this method is akin to the technology employed in solid phase micro extraction (SPME) techniques. The selective absorption/desorption of compounds can be done in a solvent-less system. Conventional SPME has not been expanded to include a large variety of different materials in which to effect the selective absorption/desorption of species.

The strategy of selectively binding to a functionalized surface a species from a mixture leads to their enrichment on the surface, generating a possible route to detection with higher sensitivity. Surface enriched laser desorption ionization (SELDI), a variation of MALDI, is based on this principle. (See, e.g., Weinberger, Electrophoresis, 6, 1164–1177 (2000)). 5–6 different surfaces can be obtained upon which protein and/or small molecules are applied, and then washed with increasing stringency. Since each surface/ stringency combination leads to a different adsorption profile, the technique provides a means for analysis of a complex mixture.

This embodiment of the invention extends this approach exponentially, by generating thousands of different surface chemistries on nanobar codes. Each chemistry is identified by its nanobar code ID; subsequent analysis by SALDI will lead to a vastly improved analysis of complex mixtures.

Combinatorially designed surfaces to capture several analytes simultaneously on distinctly coded particles from biological samples have no precedence in the separation sciences or the clinical chemistry arena. In one embodiment, to generate these surfaces, self-assembled monolayers (SAMs) may be used that are terminated with reactive functional groups are derivatized with libraries of reagents to give nanobar codes with an extraordinary variety in surface chemistry.

SAMS may be formed in a variety of ways familiar to those skilled in the art. In one example, SAMs formed from ω-carboxy substituted alkanethiols on the surface of gold have been used as model surfaces to study the interactions of proteins with surfaces. The chemistry involves capping, for example, with water soluble mercapto derivatives, typically mercapto carboxylic acid or amines. The carboxyl or amines are subsequently used to covalently label proteins, peptides or nucleic acids to give biomolecular conjugates of these particles that can be used in biological assays. Mixed SAMs have been used by others to study adsorption of fibrinogen, lysozyme, pyruvate kinase, RNAse and carbonic anhydrase.

According to an exemplative embodiment of the present invention, nanorods are synthesized possessing SAMs terminated with carboxyl functionality by reacting the rods with ω-carboxy alkanethiols. The carboxyl functionality is then activated to an anhydride for further reaction with a wide variety of amines with diverse functional groups. Another class of derivatives that would provide amine reactive functionality as well as prevent non-specific interactions with proteins are dextran lactones, easily prepared from carboxymethyl dextran. The initial derivatization of the nanorods may be done with 3-mercato propyl (trimethoxy)silane and the silane alkoxy then exchanged with the free hydroxyls of a carboxymethyl dextran derived lactone. Subsequent cleavage of the lactone with amines carrying diverse functional groups yields a library of λ hydroxy amides of dextran coated nanoparticles. These methods provide a common reactive intermediate that is easily prepared. The dextran coated or hydrophilic SAMs simultaneously provide a surface that is resistant to non-specific interaction between the nanorods and proteins having a wide range of molecular weights and isoelectric points. By appropriately choosing and designing structurally different amine reactant cocktails for derivatization, there is an opportunity to create a vast library of surfaces. These combinatorially-derivatized nanoparticles present surfaces with varying avidity for binding to the wide variety of molecules present in a biological sample, with much greater efficacy than that described for SELDI.

The affinity capture techniques with these nanorods, unlike the chip-based systems, may use off-line incubation steps for capturing the analytes. Such an approach is not only inherently superior from a kinetic viewpoint (fast capture of analytes), but is also advantageous from mass action laws to drive binding as the density of the binding determinants can be varied to accommodate a wide range of analyte concentrations encountered in a biological fluid. Carbohydrate derivatized SAMs with varying densities have been used to address issues involving cell-surface carbohydrate-protein interactions. The surfaces of this invention can be tailored to recognize free saccharides and, at the same time be designed to take advantage of multiple binding determinants for carbohydrates in glycoproteins, for example. This approach provides surfaces capable of binding a wide spectrum of molecules, from low molecular weight organic compounds to large proteins, which are addressable and amenable to analysis. Biological sources often contain a complex mixture of inorganic salts, buffers, chaotropes, preservatives, and other additives—often at higher concentrations to the molecules of interest—some of which are detrimental to the MALDI MS. This embodiment of the invention can not only generate surfaces of the same magnitude as the number of molecules present in a biological sample, but also, bind the molecules of interest to be analyzed by mass spectrometry, is essentially one of the best possible modes of sample preparation prior to analysis.

The inventors hereto are unaware of any current technology of interrogating low molecular weight organics, peptides, and larger proteins simultaneously in a microvolume multiplexed analysis. The vast library of surface modified nanorods with varying affinities for different molecules are added to a biological sample, incubated, washed, and analyzed by SALDI MS, each nanorod representing a particular molecule, the whole ensemble thereby giving a fingerprint of the sample analyzed.

Functional Proteomics

According to an additional embodiment of the present invention, the nanobar code technology may be used to: (i) develop highly sensitive multiplexed immunoassays or other forms of assays for known proteins; (ii) develop methods for identification of post-translational modifications; and (iii) study protein-protein interactions.

The primary objective of proteome analysis (a.k.a. proteomics) is the rapid characterization of gene products (proteins). State-of-the-art technology in proteomics relies on two-dimensional (2-D) gel electrophoresis that allows separation of complex protein mixtures expressed at the level of whole cells, tissues or whole organisms. After 2-D gel electrophoresis and gel staining, the revealed protein spots are excised, extracted from the gel and subjected to enzymatic digestion. The resulting peptide fragments are then characterized by mass spectrometry (MALDI-TOF MS or ESI-MS). The original protein structure can be reconstructed by matching the peptide masses against theoretical peptide masses for known proteins found in commercially available databases (e.g., SWISS-PROT.) The lack of reproducibility of the 2-D gel process, difficulties in protein quantitation, and complexities associated with sample extraction are some of the problems with this technology. 2-D gels also suffer from a separation bias against proteins of very low and very high molecular weight. Accordingly, 2-D gels are incapable of reliably profiling small organic molecules, metabolites, DNA, RNA, and, importantly, proteins below 15 kDa.

A further approach to proteomics involves limiting the analysis to known proteins (i.e. for which antibodies are commercially available). The best technique for performing proteomics based on this technology uses microspheres as the solid support; currently 100 different bead sets are available. Each bead set can, in principle, support a separate immunoassays. The data acquisition is done by an instrument similar to a conventional flow cytometer. Simultaneous quantitation of 15 cytokines has been demonstrated using this technology. A major limitation of this approach is that the frequency space of molecular fluorescence used both for microsphere tagging and detection is not wide enough to accommodate nearly as many flavors as nanobar codes (in differential reflectivity space). This presents an opportunity not only to make linear advances in this approach, but to combine the best aspects of multiplexing with the best aspects of MALDI to achieve a groundbreaking advance in proteomics.

In the proteomics field there is a need for massively parallel analysis of expressed proteins. The combination of nanobar code technology, SALDI and fluorescence based immunoassays into one platform, as described below, enables the generation of highly sensitive and quantitative multiplexed immunoassays for known proteins. The ability exists to merge selectivity, sensitivity, multiplexing, quantitation and mass analysis in the same measurement, offering among other benefits a minimum of 100-fold increase in sensitivity.

First, a specific immunoassay is associated to each flavor of nanobar code, via attachment of a specific capture antibody. Analyte is bound to the antibody-coated nanorod and is detected with a second antibody tagged with a fluorescent dye, which recognizes a different epitope on the analyte.

This process can be done in the same sample for as many proteins as there are both capture and detection antibodies available; several hundred pairs of antibodies are currently commercially available, and this number will grow in the future. Moreover, other approaches to protein assays (such as aptamer technology and phage display) are currently being developed and improved. Thus, the method has the capability to interrogate simultaneously the biological sample for the presence of all known proteins which appropriate selective binding chemistry exists (or will exist). A benefit of this system is that even greater multiplexing is possible with two or more fluorophores.

Post-translationally modified proteins (good candidates for new disease markers) may be detected using the same platform. Any protein can be subjected to co- and post-translational modifications. These modifications have an influence on the charge, hydrophobicity, conformation of the "parent protein", and can occur at different levels. Modifications like acetylation, phosphorylation, methylation, hydroxylation, N- and O-glycosylation can occur at the cellular level as well as in the extracellular fluids. There are now over 100 known post-translational modifications To detect post-translational modification, polyclonal antibodies raised against a protein are conjugated to a specific bar code flavor. The polyclonal antibody will capture not only the protein against which it has been raised, but also protein isoforms (that share similar epitopes but are modified at different sites). If the isoform is recognized by the detection antibody, it will be quantitated along with the "parent protein" (i.e. by the fluorescence immunoassay). If post-translational modification has affected the epitope that is recognized by the detection antibody, the isoform will not be quantitated by fluorescence. If both the capture antibody and the detection antibody are polyclonal antibodies, there is a good chance that a great number of the modified proteins will be quantified. After the fluorescence measurement, the nanorods are subjected to mass spectrometry analysis. SALDI-MS is used to characterize the protein and identify the different post-translation modifications. The SALDI-MS laser energy ruptures all non-covalent bonds allowing for detection of any molecule complexed on the nanorod, including even the protein sandwiched by two antibodies.

The tagging of an assay with a specific nanobar code is critical to the success of this method. The code on the bar will be associated with a specific predetermined protein having a specific molecular weight. When this nanorod is analyzed, instead of a full scan analysis, the mass spectrometer can be tuned to concentrate on a particular mass by using a technique called Single Ion Monitoring (SIM). SIM mode allows faster acquisition of data and increases the analytical sensitivity (up to 1000-fold enhancement in detecting an ion in SIM mode versus detecting this same ion in full scan mode). With the knowledge of the expected mass (and the sequence) of the analyte, the mass analyzer can be focused on a mass range allowing the detection of all the possible isoforms related to the parent protein. The monitoring range could be set to the molecular weight of the parent+/−500 Da for example. Determination of the molecular weight of the isoform will reveal immediately the modifications that the parent protein has suffered. Thus, the combination of nanorods and polyclonal antibodies has the advantage of localizing the parent proteins as well as the corresponding isoforms on one flavor of nanorods. The nanorods allow for a connection between the "parent protein" and the corresponding isoforms. This is not the case for 2-D gel electrophoresis where the post-translationally modified protein can "appear" in a different place of the gel if the charge has changed (following phosphorylation, for example). In short, 2-D gel requires a large amount of additional effort (i.e. sequence determination) for the identification of the modified protein since the connection between proteins of the same family is missing.

Other approaches to detect post-transitional modifications are also possible. For example, chemistries may be developed that recognize all post-transitional modifications of a various type, e.g., a nanobar code can be functionalized to recognize all proteins that have been myristlyated, another could bind to all glycosylated species, etc. The collection or assembly of such nanoparticles can thus be a probe of overall post-translation modification. Analysis of absorbed species on each nanobar code can be conducted by any appropriate means, including mass spectrometry. Importantly, even when the exact chemical nature of the individual species are not ascertained, there is value in knowing the total amount of post translational modifications. The amount of post translational modifications can be a measure of stress and, therefore, overall health.

Protein-protein interactions are examined according to the present invention by binding specific proteins to nanorods for screening the biological sample for potential entities capable of molecular recognition. Nanorod technology combined to fluorescence-based quantitation and mass spectrometer-based identification allows investigation of specific protein-protein interactions. Different assay formats are used to interrogate the biological sample for the presence of free analyte A or for the presence of the free receptor R for analyte A. These two formats have been described above. Another set of nanorods labeled with antibody directed against A can be used to quantify analyte A bound to its receptor R by using a detection antibody directed against the receptor. Similar assays can be set-up in which free auto-antibodies and auto-antibodies binding analyte A can be quantified using a fluorescent anti-Fc antibody, for example.

As described above, the nanorods are analyzed by SALDI-TOF MS to allow identification of the different isoforms present. Where no detection antibodies are available, SALDI-TOF is still able to identify and characterize the different components. Quantitation by fluorescence will be missing but identification by mass spectrometry of the captured analyte is possible. Alternatively a nanorod labeled with any protein can be used to screen the biological sample for the presence of a protein or any other entity having any affinity for the nanorod conjugated protein. The presence of the bound protein will be detected by mass spectrometric analysis.

All conceivable ligands that have been used in affinity chromatography and all stationary phases that have been used in thin layer chromatography, HPLC or gas chromatography, may be used to label nanorods, and all could be combined in one single tube containing a minimum volume of biological sample. Because of the size of the nanorod, sample size will be greatly reduced compared to currently developed protein arrays. The table below lists examples of ligands that may be used for nanorod derivatization to capture (extract) specific molecules (counterligands) from the biologic sample.

Examples of Ligand/Counterligand Pairs that can be Utilized for Nanorod Capture

| LIGAND | COUNTERLIGAND |
|---|---|
| Cofactors | Enzymes |
| Lectins | Polysaccharides, glycoproteins |
| Nucleic acid | Nucleic Acid binding protein (enzyme or histone) |
| Biomimetic dyes | Kinases, phosphatases, Dehydrogenases etc. |
| Protein A, Protein G | Immunoglobulins |
| Metals ions | Most proteins can form complexes with metal ions |
| Enzymes | Substrate, substrate analogues, inhibitor, cofactors |
| Phage displays | Proteins, peptides, any type of protein |
| DNA libraries | Complementary DNA |
| Aptamers | Proteins, peptides, any type of protein |
| Antibody libraries | Any type of protein |
| Carbohydrates | Lectins |
| ATP | Kinases |
| NAD | Dehydrogenases |
| Benzamide | Serine Protease |
| Phenylboronic acid | Glycoproteins |
| Heparin | Coagulation proteins and other plasma proteins |
| Receptor | Ligand |
| Antibody | Virus |

Finally, it should be noted that this method allows for a significant reduction in sample size, via addition of thousands of different flavors of nanobar codes to a few microliters or less of a biological sample. This is an advantage over the use of biochips or arrays where antibodies or proteins are spatially arranged on a flat surface. In the latter case much higher sample volume is required to contact the entire chip. In addition, if the nanoparticle has a magnetic metal, they can be pulled out of solution by magnetic interaction.

For proteins up to mass 13 kDa, SALDI mass resolution is similar to MALDI. Between 17–30 kDa, mass resolution in SALDI drops by a factor of 2–3. Nanobar codes have the required spectral properties to allow proper energy transfer to the adsorbed proteins. By varying the width of the different Au segments, the nanobar code spectral properties can be tuned to deliver the optimum protein desorption and ionization energy.

Phenotyping

The Nanoparticles of the present invention can be used as a platform for multiplexing assays in very small volumes of biological sample. This platform allows simultaneous measurement of over many hundreds or thousands of assays from ultra small volumes of biological samples.

Today, a large number of independent and different measurement techniques are used to characterize the metabolism and physiology of humans or large animals. Phenotyping of small animals is practically impossible due to the limited availability of large tissue volumes. The present invention has the unique capability of not only combining many of these measurements on one platform, but also confining all these measurements in the same minute sample volume. This makes this platform extremely attractive for the measurement of multiple analytes in scarce biological samples (i.e. plasma from small animals).

This embodiment of the invention will specifically focus on:

1) The development of a platform allowing optical interrogation of nanobars.
2) The readout of multiplexed immunoassays and feasibility of mouse phenotyping.

Cylindrically-shaped colloidal metal nanoparticles of the present invention will be used in which the metal composition can be alternated (e.g., Pt/Au/Pt/Au/Pt) along the length, and in which the metal segments can be length-tuned. These nanobar codes will serve as solid phase identity tags for the immunoassays to be developed. In a typical sandwich immunoassay, the capture antibody will be conjugated to a specific nanobar code and the corresponding detection antibody will be labeled with a fluorophore.

A reader can be used capable of imaging the intrinsic differences in reflectivity of the metal segments in individual bars by conventional optical microscopy. This reflectivity measurement permits nanobar code identification while the fluorescence intensity associated to the corresponding nanobar via binding of the detection antibody will determine the concentration of the analyte. Software that can automatically analyze reflectivity images and identify nanobar codes as well automatically analyze fluorescence images and quantify nanobar code fluorescence can be used. The development of sandwich immunoassays will demonstrate parallel acquisition of reflectivity data and fluorescence detection data.

Finally, in a very small plasma volume (50 microliters or less), assay multiplexing can be shown for a large panel of proteins relevant for the physiological characterization of an organism. The ability to conduct a large number of assays from a sample volume is critical in many animal studies, particularly for often-used mice studies. 50 microliters of plasma can be harvested from a mouse without harm to allow multiple longitudinal blood draws and repeated measurements over the life of the mouse. This protocol enables, for example, the fully automated, integrated and simultaneous measurement of cytokine, auto-antibody, general protein and hormone profiles in the same tissue sample.

Phenotyping takes on particular relevance with respect to animal models for human disease. Whether the model is the zebrafish, the rabbit, or the mouse, the ability to knock in or knock out individual genes or sets of genes is a powerful approach to generation of strains engineered to study disease progression. Likewise, animal models present a convenient vehicle for monitoring therapeutic response. At the same time, phenotyping in animal models presents an extraordinary bioanalytical challenge: in addition to seeking to measure "everything," the amount of tissue available for these studies is small. For example, one can only expect to get about 200 microliters of blood from a mouse tail bleed. Moreover, while PCR amplification converts vanishingly small amounts of DNA into analytically useful quantities, techniques in current practice for proteomics, including 2-D gel electrophoresis and the surface-affinity based methods, require very significant amounts of sample, and moreover do not yield high resolution separations. For small molecule assays, small volume methods to profile a wide variety of metabolically relevant species have not been demonstrated: to the contrary, the focus of pharmacokinetic studies with the pharmaceutical community has almost exclusively centered on the fate of one or a few species.

The solution to this problem is to carry out multiple, high sensitivity measurements simultaneously, and two approaches have been widely used. Arraying involves spatial separation of the various chemistries under investigation in different locations that can be probed individually. The gene chip does this for oligonucleotides (see, e.g., Michael et al. Anal. Chem. 70, 1242–1248 (1998)) and the same strategy is being carried out, at a very rudimentary level, for proteins. Multiplexing refers to making multiple independent measurements at the same time and/or in the same region of space and/or using the same materials. This can occur on a chip, as in current approaches to analysis of gene expression, where the relative levels of expression of cDNA from two samples of DNA labels with different fluorophores is measured. This strategy has been adapted to proteomics, by derivatizing two protein samples with different fluorophores and mixing prior to separation by 2-D gel electrophoresis. In these cases, the level of multiplexing is only two, affording minimal increases in efficiency. Using the nanobar code particles of the present invention, any capture chemistries known to those skilled in the art can be used. This provides for multiplexing that can be done on an unparalleled scale.

Non-Bioanalytical Applications of Bar Coding

In the twenty-five years since bar coding was introduced, most major industries worldwide have grown to recognize the benefits of the technology and its use has expanded. For example, the grocery industry has moved beyond scanning at point of sale and now uses bar coding throughout the supply chain from the manufacturing, distribution and selling processes until the item reaches the customer. Although industries look for specific benefits, the general benefits of bar coding include increased accuracy, improved productivity, improved quality and cost savings. The sale of bar coding equipment is a $4 billion a year market in the US alone; the value of the material that is bar coded is far greater. However, despite increased use and improvements in technology, many industries are not able to exploit bar code technology due to physical or environmental constraints. Examples include the small size of the item to be bar coded (e.g. fasteners), the material on which bar codes must be applied (e.g. curved metallic surfaces), where bar codes interfere with the item or its function or use (e.g., works of art), or the processes (e.g. extreme heat or extreme cold) an item goes through either in the manufacturing or distribution of the product or in actual use (e.g. paint). Nanobar codes create enabling capabilities in several of these areas. Moreover, it is important to stress that the durability (and chemical inertness) of these materials contrasts sharply with other types of paper or plastic tags.

The use of nanobar codes as tags or labels can be further extended by the use of multiple particles as a label. By using a plurality of tags to label a material, the number of different types of nanobar code particles that have to be prepared can be reduced, while still providing the same large numbers of distinctly identifiable combinations of nanoparticles.

Unit Dose Medications in the Healthcare Industry. Healthcare is a global industry with similar issues and needs in every country. Worldwide the industry is under extreme pressure to reduce costs. In the United States alone in 1995 expenditures for healthcare totaled $1.5 trillion. The Efficient Healthcare Consumer Response (EHCR), published in 1996, concluded that bar coding and automation could save $11 billion per year in three product categories: non-capital medical/surgical supplies, non-capital diagnostics, and non-retail ethical pharmaceutical products. The industry has made good progress in the labeling of cartons and boxes of products but continues to struggle with small items such as unit dose medications. Bar coding of these items is particularly important, given that the Institute of Medicine recently revealed that 44,000 to 98,000 people a year might die because of medical errors that occur in U.S. hospitals.

Fastener Industry. The United States imports $7–$8 billion of fasteners (nuts, bolts, screws, rivets, washers, etc.) each year. These products are then repackaged and sold through a variety of methods of distribution into major industries such as aerospace, automotive, nuclear, commercial and electrical creating an estimated $30–$40 billion market. Over the last several years the product packages have been bar coded. However, individual fasteners are not.

The industry experienced a serious risk and liability problem several years ago as bogus fasteners of inferior quality entered the market place. To combat the problem, bar coding on product packages was introduced and the Fastener Quality Act was developed. This Act was finalized in December 1999. There are requirements for fasteners used in "critical applications", including compliance with laboratory tests standards of hardening through heat processing. However, a problem still exists, in that while packages of fasteners can be labeled, individual fasteners cannot be marked. Nanobar codes on fasteners provides the industry with the means to comply with the Fastener Quality Act and vastly improve human safety and reliability issues.

Tires. The industry has long sought a solution for tracking individual tires. This is especially true for the commercial (truck) tire business. Truck tires are frequently re-treaded two or three times and put on a different axle of the truck. Although the economic and safety incentives are there, today there is no easy or cost effective way of identifying a specific tire so that usage and maintenance can be monitored. Commercial tires are a $6–$8 billion dollar/year business. (New tires cost approximately $300; retreading approximately $90 per tire.) There are approximately 7 million tires sold for new equipment, 14 to 14.5 million sold for replacement tires and an additional 15 million retreaded tires annually. With nanobar codes, records for each tire can be maintained assuring that tires are maintained and used in a way to assure safety. Successful application of nanobar codes in the commercial tire industry will likely lead to penetration in the automotive tire business as well.

Weapons Tracking. There is great controversy over hand gun control. One level of the controversy involves a practical method for making handguns traceable. Nanobar codes can make it possible to identify a specific gun, the clip, the firing pin and even shell casings. This could significantly improve traceability and make compliance with state and federal regulations more feasible as well as assist in foreign identifications investigations and law enforcement. Likewise, the tracking of explosives can be followed by incorporation of bar codes. Currently, the Department of Energy has an explosives classification tracking system (http://faxback.wmnsnw.com/ects/summsrch.asp), but has no mechanism for directly tracking the thousands of known explosives. It is significant that nanobar codes appear to satisfy all the criteria listed by the National Academy of Science's Committee on Marking, Rendering Inert, and Licensing of Explosive Materials. These criteria include safety in manufacture and use, effect on the performance of explosives products, utility for law enforcement, forensic and prosecutorial utility, blast survivability, environmental acceptability, cost, and universal applicability.

Money and Legal Documents. Although many steps have been taken to assure that money and documents such as passports and visas can't be counterfeited, invisible (to the naked eye) nanobar codes can be used in the paper to assure the authenticity of the document. Moreover, conventional bar codes can be used as positional indicators of nanobar codes. In other words, documents could be impregnated with nanobar codes in specific locations that are revealed by interrogation of the macroscopic bar codes. This will allow rapid verification of document authenticity.

Paint. Bar coding of paints, a $16 billion/year business in the US in 1997, offers three excellent opportunities. (1) Outdoor architectural paints. Traditional forms of bar coding cannot be used because of the lack of durability, and because their size adversely impacts formulation. Introduction of nanobar codes into outdoor paints allows the paint age to be tracked, and for public, rust-sensitive structures (such as bridges), will allow for preventive maintenance. (The same can be said for nanobar codes in concrete and pavement). (2) Indoor architectural paints. One problem many homeowners often face is the lack of traceability of previously applied, formulated (i.e. mixed) paints: it is typically impossible to exactly reproduce such mixtures. Vendors of paint that offer a bar coded product that will allow the exact formulation to be prepared many years after the original formulation will have a large competitive advantage. (3) Nanobarcoding of priceless art will render forgeries easy to distinguish. Indeed, individual artists may choose to incorporate their own "individualized" bar codes to all their products to guarantee long-term authenticity.

Electronic Devices

A straightforward extension of making bar-coded multi-metallic rods is to form active and passive electronic devices, which can function as components of nanoscale and microscale electronic circuits and memories. These structures could include such standard electronic devices as wires, resistors, capacitors, diodes, and transistors. They could also be devices with more complex electronic functions, such as negative differential resistance (NDR) devices, resonant tunneling diodes, ferroelectric switches, shift registers, and delay lines.

Resistors can be fabricated by growing a resistive component (e.g., a polymer) between two conductive metal stripes (e.g., gold, copper, or silver). Polymeric molecules of this type include conducting polymers, such as poly(pyrrole), poly(aniline), and poly(thiophene), and dielectric polymers such as poly(allylamine hydrochloride) and poly(dimethyldiallylammonium chloride). Thinner stripes of more highly resistive materials, such as self-assembling monolayers, which are typically monomeric organic molecules that are functionalized at one end with a thiol, isonitrile, carboxylate, or other ligating group, can also function as resistive elements.

The present invention also allows for the synthesis of nanoparticles that can be used in diode and negative differential resistance structures.

A. Metal-semiconductor-metal devices. These devices consist of a multicomponent rod with metal ends and a semiconductor particle in the middle. The metal ends can be made by conventional electroplating or by electroless plating, and the semiconductor can be a pure element, such as silicon, germanium, tin, or selenium, or a compound semiconductor such a metal oxide, metal sulfide, metal nitride, metal phosphide, or metal arsenide. Rods have been made with diameters varying between 70 and 200 nm which contain oxide semiconductors (titanium dioxide or zinc oxide) and chalcogenide semiconductors (cadmium selenide) between two metal ends. The diameter of the semiconductor "stripe" is typically the same as the rest of the rod, and its width varies from a few nanometers to 1–2 microns. The metals used to date in diode rods include gold, silver, platinum, and nickel, but could in principle be any of the metals described elsewhere in this invention. The semiconductors can be introduced into the membrane pore template by adsorption of colloidal particles, or by electrochemical growth. The top metal contact is fabricated by electrochemical deposition and by electroless deposition. Such diodes generate an asymmetric current-voltage curve. Both symmetric structures (e.g., gold-cadmium selenide-gold) and asymmetric structures (gold-silver-zinc oxide-gold) have been found to have rectifying current-voltage characteristics.

B. Metal-molecule-metal devices. Instead of incorporating a semiconductor particle into a striped rod structure, it is possible to use a molecular layer, which can be deposited either electrochemically or by self-assembly. This molecule can be a conducting or dielectric polymer, as described above. Other examples include self assembling monolayers. The interface between the molecule and the metal can be rectifying or have other electronic characteristics, such as negative differential resistance. For example, we have shown that gold-molecule-nickel devices, in which the molecule is 16-mercaptohexadecanoic acid, have current rectifying characteristics. Negative differential resistance molecule I has also been incorporated into such a structure. The molecular layer is typically very thin (0.5–3 nm), and can be introduced by adsorption onto the bottom metal, followed by electrochemical or electroless deposition of the top metal. Alternatively, a striped rod containing a suitably thin sacrificial metal layer (such as copper or silver) can be immobilized on a surface or in a circuit, and then etched chemically or electrochemically to leave a gap between the end metals. The gap can then be filled by electrochemically depositing or adsorbing a polymer or monomeric molecule from solution, or by thermally evaporating a volatile molecule.

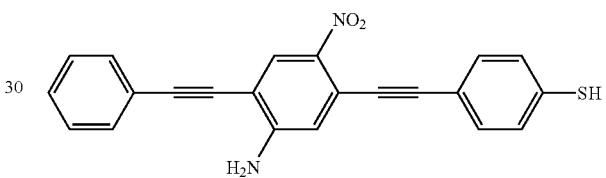

I

By applying a gate lead to either of the diode devices described above, it is possible to make a device that functions as a transistor. Such a lead could be applied in a crossbar structure, which can be fabricated by electric field-driven assembly or by self-assembly.

A high aspect ratio rod containing multiple stripes of conductive metals and other materials (polymers, semiconductors, or inorganic or organic dielectrics), could function as a delay line or shift register if a train of high and low voltage pulses is applied at one end. If the rate of propagation of the voltage from one end of the rod to the other is slow compared to the clock frequency of the circuit used to apply the voltage pulses, then the signal could be read out at the other end as a string of zeroes and ones.

EXAMPLES

The following examples are provided to allow those skilled in the art access to information regarding various embodiments of the present invention, and are not intended in any way to limit the scope of the invention.

Example 1

One embodiment of the present invention is directed to the template-directed synthesis of multiple flavors of nanobar codes for the purpose of multiplexed assays. For this application it is desirable to construct a variety of different flavors which are easily distinguished by optical microscopy. For example, 10 different flavors of nanobar codes were synthesized according to the table below, using gold and silver segments. Note that the description field of the table indicates the composition of each nanobar code by segment material and length (in microns) in parentheses. For example, Flavor #1 is 4 microns long gold, and Flavor #2 is 2 microns gold followed by 1 micron silver, followed by 2 microns gold.

| Flavor # | Description | # Segments | Length |
|---|---|---|---|
| 1 | Au (4) | 1 | 4 µm |
| 2 | Au (2), Ag (1), Au (2) | 3 | 5 µm |
| 3 | Au (1), Ag (1), Au (1), Ag (1), Au (1) | 5 | 5 µm |
| 4 | Au (2), Ag (2) | 2 | 4 µm |
| 5 | Ag (1), Au (1), Ag (1), Au (1), Ag (1) | 5 | 5 µm |
| 6 | Ag (1), Au (4) | 2 | 5 µm |
| 7 | Ag (4) | 1 | 4 µm |
| 8 | Ag (1), Au (2), Ag (1) | 3 | 4 µm |
| 9 | Ag (1), Au (1), Ag (1), Au (2) | 4 | 5 µm |
| 10 | Ag (2), Au (1), Ag (1), Au (1) | 4 | 5 µm |

A detailed description of the synthesis of Flavor #4 follows. (All other flavors were synthesized by minor and obvious changes to this protocol.)

25 mm diameter Whatmnan Anopore disks with 200 nm diameter pores were used for template directed nanobar code synthesis. Electrochemical metal deposition was carried out using commercially available gold (Technic Orotemp 24), and silver (Technic ACR 1025 SilverStreak Bath) plating solutions. All of the electroplating steps described below were carried out in an electrochemical cell immersed in a sonication bath, which was temperature controlled to 25° C.

The synthesis of nanobar code Flavor #4 was carried out as follows. The membrane was pretreated by evaporating ~500 nm of silver on its branched side. To completely fill the pores on this side, approximately 1 C of silver was electroplated onto the evaporated silver, using 1.7 mA of plating current for approximately 15 minutes. Then an additional 1 C of silver was electroplated into the pores of the membrane from the side opposite the evaporated silver, using 1.7 mA of plating current for approximately 15 minutes. This silver layer is used to fill up the several micron thick "branched-pore" region of the membrane. The silver plating solution was removed by serial dilutions with water, and was replaced by the gold plating solution. The 2 micron long gold segments were then deposited using 1.7 mA of plating current for approximately 30 minutes. The gold plating solution was removed by serial dilutions with water, and was replaced by the silver plating solution. The final 2 micron long silver segment was then deposited using 1.7 mA of plating current for approximately 30 minutes. The membrane was removed from the apparatus, and the evaporated silver layer (and the electrodeposited silver in the branched pores) was removed by dissolution in 6 M nitric acid, being careful to expose only the branched-pore side of the membrane to the acid. After this step, the nanobar codes were released from the alumina membrane by dissolving the membrane in 0.5 M NaOH. The resulting suspension of nanobar codes were then repeatedly centrifuged and washed with water.

Example 2

It is an important goal to demonstrate the ability to use a wide number of materials in the nanobar codes of the present invention. To date, rod structures formed by electrochemical deposition into a membrane template (alumina or track etch polycarbonate) include Ag, Au, Pt, Pd, Cu, Ni, CdSe, and Co. Primarily, the 200-nm diameter alumina membranes have been used for convenience. Many of the materials are now also being used in the smaller diameter polycarbonate membranes.

CdSe is currently plated via a potential sweep method from a solution of $CdSO_4$ and $SeO_2$. Mechanical stability problems have been encountered with the metal:CdSe interface; i.e. they break when sonicated during the process of removing them from the membrane. This has been remedied with the addition of a 1,6-hexanedithiol layer between each surface. The Cu and Ni are plated using a commercially available plating solution. By running under similar conditions as the Ag and Au solutions, it was found that these metals plate at roughly the same rate, ~3 µm/hr. The Co is plated from a $CoSO_4$/Citrate solution. These rods seems to grow fairly monodispersely, however they grow comparatively slowly, ~1.5 µm/hr.

Example 3

The orthogonal functionalization of Cu and Ni nanobar codes is accomplished using on the Cu, benzotriazole and butylcarbamate, and on the Ni, dimethylglyoxime and hydroquinone. The rods are composed of Au ends with Cu or Ni middles. 1,6-hexanedithiol and 2-mercaptoethylamine are used to functionalize the ends of the rods. Benzotriazole is a compound that is typically used for corrosion inhibition for copper, meaning it should be able to bind effectively to the copper section of the rod. Butylcarbamate is a molecule with a terminal carbonyl and amine group on the same end, both of which chelate Cu well. The glyoxime and the hydroquinone are also known to chelate Ni, making them a good functional group for monolayer formation. These are combined in various ways to produce the best results for orthogonal functionalization. It is possible to exploit the differential binding equilibrium constants and order of exposure to create a large variety of orthogonally functionalized segments. The rods are then functionalized with rhodamine or fluorecin to determine the presence of exposed amine and thiol functional groups respectively. Depending on the dye and the surface functionalization it is possible to make various parts of the rods "light up".

Example 4

A solution based sandwich immunoassay has been developed for use on bar code rods that employs optical microscopy fluorescence detection. The assay has been performed on Au, Au/Ag and Au/Ni rods of varying segment patterns. The nanobar code is read based on differences in reflectivity of the metals at differing wavelengths. FIG. 4 depicts the results of this experiment.

Initially, the sandwich immunoassay was performed on two types of rods, Au/Ag and Au rods, using the following system: anti-rabbit IgGFc/rabbit IgG/anti-rabbit IgGH&L labeled with Texas Red. Fluorescence images have been taken with filters for FITC on a mixture of rods and the rods appear to be the same metal composition with a 600 nm bandpass filter, however, changing to a 400 nm bandpass filter reveals the bar code ID.

Then two different sandwich immunoassays were performed on two different types of bar code rods. For this experiment the same Texas Red (TR) assay as mentioned above was used along with the following system: anti-human IgGFc/HIgG/anti-human IgGg specific. FITC images were taken first since this fluorophore photobleaches much quicker than TR. Since it was established that at least two fluorophores could be distinguished, a simultaneous solution based assay was attempted next. The rods were derivatized with the capture antibody in separate tubes after which they were mixed together for completion of the assay in order to mimic conditions present in serum samples. Two fluorophores were necessary to determine the amount of non-specific binding as well as cross-reactivity. Initially, there was a significant amount of cross-reactivity between the two systems as well as some non-specificity to the rod surface. To circumvent this problem, an amino terminated PEG was used, which significantly cut down on non-specificity, and BSA was used to help with cross-reactivity. The simultaneous, solution based two-system sandwich immunoassay was successfully completed. 4 µm Au/Ag/Au rods were derivatized with a-human IgG, (FITC); and 8 µm Au/Ni/Au were derivatized with a-rabbit IgG (TR). The Au sections of the Au/Ni/Au rods were selectively derivatized as evidenced by the lack of fluorescence on the Ni sections. Furthermore, Ag appeared to enhance fluorescence from FITC.

To investigate the enhancement factors of Ag with FITC, a sandwich assay was performed using two different fluorophores on the same type of rods. The human IgG FITC system and a new system of the following: anti-Cytochrome c/biotinylated Cc/streptavidin-phycoerythrin (PE) was used. As for the human IgG system, there was brighter fluorescence on sections of the rod which correspond to the Ag sections, as revealed in the reflectivity image. However, no enhancement from Ag was seen for the PE system. Thus, it is likely that the enhancement is a wavelength specific phenomena, both with respect to the fluorophore absorbance and the nanobar code extinction (absorbance and scattering).

Example 5

Flow cytometry experiments have been employed to quantitate fluorescence from immunoassays or nanobar codes. Both human IgG and biotinylated Cc systems have been investigated. The rabbit IgG system was switched to the biotinylated Cc system because TR could not be excited with 488 nm in the flow cytometry instrument. Titration curves were prepared for the human IgG and the biotinylated Cc systems on Au/Ag nanobar code. From the graphs, it appears that the titration curve for human IgG contains an inflection point, whereas the biotinylated Cc system does not. Instead, it reaches a maximum and appears to level off. The shape of the curve for the human IgG system may originate from Ag enhancement of FITC. Flow cytometry experiments may be conducted to determine the amount of antibody binding capacity (ABC), as well as the concentration of capture antibody needed to optimize the system.

Example 6

The use of colloidal Au or Ag for detection of bioassays has been studied. This relates to the differences in reflectivity of metals at different wavelengths. In theory, the bar code ID, or portions thereof, would not be visible at the reflectivity isosbestic, i.e. about 600 nm for Au and Ag. However, selectively placing colloidal particles on all or part of the bar code would result in a reflectivity change, hence a reflectivity contrast. Colloidal Au particles are best for this aspect since they are easier to make monodisperse, derivatize, and biocompatible. A preliminary experiment has shown that adsorption of a layer of Ag colloid can alter the reflectivity of Au/Ag rods. This was accomplished by adsorbing a monolayer of 1,6-hexane dithiol on the rods followed by exposure to Ag colloid. TEM data confirms binding of colloidal Ag to the nanobar codes. At 400 nm, the characteristic striped pattern of reflectivity can be seen with or without addition of colloidal Ag. However, at 600 nm, the striping pattern cannot be seen in the absence of Ag nanoparticles but can be seen in the presence of Ag nanoparticles.

These data indicate that there is a differential electromagnetic interaction between the Ag nanoparticles and the Ag and Au segments of the nanobar code, since the TEM data indicate a uniform distribution of the Ag material over the surface of the nanobar code. Note that the changes in reflectivity do not need to involve an isosbestic (i.e., from no differential reflectivity to differential reflectivity or visa versa). All that is required is that a chemical or biochemical event be coupled to a change in reflectivity. Moreover, this change in reflectivity does not need to be different for the various segments. Thus, the most general implementation involves a molecular binding/debinding induced change in reflectivity of one or more segments for the entire nanobar code. A more specific embodiment involves changes in reflectivity leading to elimination (or generation) of a reflectivity isosbetic.

Example 7

Bar code rods are useful for solution based assays methods for the detection of DNA hybridization or dehybridization. Initially, oligos are used for method development, however the technology can easily be extended to cDNA's. To date, the attachment of short oligos (12-mers) to rods has been accomplished using fluorescence (FITC) for detection. Two methods of attachment, both of which employed amino modified oligos, have been performed. One method used a bifunctional crosslinker, 1,4-phenylene diisothiocyanate (PDITC), to link the amino modified oligo to a layer of amino terminated PEG. The second method employed traditional carbodiimide coupling to attach the amino modified oligo to an adsorbed layer of "amino acid" PEG (HCL $NH_2$-PEG-COOH). Traditional carbodiimide coupling yields a higher amount of attachment than does the bifunctional crosslinking method. Furthermore, carbodiimide coupling is easier to do, can all be done in aqueous solution, and is more reproducible. Any additional form of attachment known to those of skill in the art can also be utilized.

Example 8

This example relates to the DNA-based assembly of noble metal nanorods with the ultimate goal to use DNA to assemble the particles into functional, sublithographic, electronic devices. It is important to understand how thiol functionalized DNA attaches to colloidal sols of these rods, and how to apply this knowledge to the assembly of the rods.

Much of this effort focuses on using DNA to assembly nanometer scale Au particles. Before these particles can be assembled using DNA, it is essential to understand the fundamental process of derivatizing the particles with DNA. The adsorption thermodynamics of DNA onto these particles and the hybridization efficiency of the DNA once it has been assembled on the surfaces of these particles has been studied. A Langmuir adsorption isotherm has been prepared for the adsorption of thiolated and nonthiolated DNA (36 bases in length) onto a colloidal sol of Au nanorods. (200 nm×3 µm). Using these plots, $\Delta G$ values can be calculated for both the adsorption of both thiolated and nonthiolated DNA onto the particles, $-1.83 \times 10^5$ J/mol and $-2.51 \times 10^4$ J/mol, respectively.

The ultimate goal of this embodiment of the invention is to use DNA to assemble nanorods on patterned surfaces to form a memory device. Before assembly can begin on a patterned surface, it is important to understand assembly on a simpler system, for example, on Au films. A variety of parameters have been explored to study their impact on the assembly of rods, including, salt concentration, temperature, blocking agents, and three oligo systems versus two. The best results have come from derivatizing the rods with thiolated DNA followed by immersion in 6-mercaptohexanol. A Au film is then derivatized in thiolated DNA followed by octanethiol. The rods are then suspended in a buffer that is 10 mM phosphate (pH=7), 0.5% Blotto blocking agent, 1 mM sodium dodecylsulfate, and 50 µM junk oligonucleotide. The Au films are then immersed in this solution and tumbled overnight. Using this system, the number of rods assembled has been greatly increased while the number assembled nonspecifically has been decreased.

An alternative derivatization involves using functionalized PEGs to attach the DNA to the surface of either the nanorod or the Au surface or both. This technique involves placing the rod or Au surface in the following solutions: 16-mercaptohexadecanoic acid, EDC/NHS, aminated PEG, 1,4-phenylene diisothiocyanate, aminated DNA. This derivatization strategy did little to improve the assembly of Au rods on Au films, but dramatically improved their assembly on patterned Au surfaces on Si, especially when a succinic anhydride functionalized silane was used to derivatize the Si surface. The succinic anhydride can then be treated with water, leaving negatively charged carboxylate groups on the Si surface that repel the anodic DNA-coated nanorods.

Example 9

Most rod experiments have been performed using 200 nm diameter rods that were grown in commercially available alumina membranes. There have also been efforts to use smaller diameter, polycarbonate membranes. The rationale for this is that certain optical properties or magnetic properties, or physical or chemical properties or assembly chemistries will be superior for use with smaller particles. Rods containing Au and Ni stripes have been derivatized with Ni chelating agents (dimethylgyoxime or 8-hydroxyquinoline). The rods can then be immersed in a thiol solution of interest, and the thiols will assemble on the Au as desired while the Ni stripes are effectively "blocked" from the thiol. Rods were derivatized with dimethylgyoxime, followed by thiolated DNA. The rods were then treated with YOYO, a DNA intercalating dye that also binds to single stranded DNA. These data show that orthogonal derivitization can be extended to include Au/Ni (as well as Pt/Au as discussed above). Nanobar codes containing Au/Ni/Pt should allow three different chemistries to be placed on the sane nanoparticle. It is likely that selective chemistries can be developed for copper (e.g., employing dithiocarbamates). Thus, it should be possible, for example, to attach four separate oligonucleotides to a single nanoparticle, each differing at one base residue. Such a system would tremendously simplify SNP analysis. With four types of segment material chemistries combined with end or tip derivitization, a single nanobar code could be derivitized with at least six different chemistries in specific locations.

Example 10

Electric fields to align particles have been successfully used. In this experiment the effects this field alignment has on the surface chemistry of the aligned rods is studied. Rods were derivatized with mercaptoethylamine and then aligned by electric field. They were then returned and immersed in a solution of rhodamine B isothiocyanate. The surfaces were then imaged under a fluorescent microscope. Several alignment potentials and frequencies were investigated until one was discovered that did not oxidize the thiols off of the surface of the rods.

Example 11

Efforts have been made to manipulate ordered two-dimensional structures of metal nanorods. Viable means are sought to assemble discreet packets of rods. Two-dimensional assemblies of four or more rods (the width of which is shorter than the length of the rods used in a given assembly) are to be created and placed in defined (or accessible) locations. This assembly type may then serve as the bottom third of a cross bar structure and aid in the assembly of upper layers. The second layer is an electronically definable memory element, and the third is another two-dimensional rod assembly that is rotated 90° with respect to the first. The first layer could aid in construction of the other two layers by utilizing multimetal striping and complementary surface chemistry.

Rod Bundles Formed at Interfaces

Rod raft formation techniques were attempted that involved chemically modifying Au rods (250 nm diameter) of various lengths with polyelectrolytes or thiols. The modified rods were typically in water and were then mixed with a dissimilar solvent, such as hexane. Rod rafts of various organizations would then assemble at the interfacial region of the two solvents. These rafts could then be removed from the interface and placed on a solid substrate for further analysis and manipulation.

In trying to form smaller groups of rods, the concentration of rods was decreased in the aqueous phase as well as different solvents to create interfaces. The surface modification that seemed the most promising is Au rods modified with mercaptoethane sulfonic acid (MESA) and the polyelectrolyte polyallylamine hydrochloride (PAH). Smaller rods packets are formed; however, many single rods and disorganized groups are present. Several small bundles of PAH rods at water/hexane are formed with relatively few single rods. This particular sample was transferred to a glass surface. Further layering of polyelectrolyte (polystyrene sulfonate (PSS) and PAH) was used to strengthen the rod packets. The rods were then removed from the surface and transferred to solution. These rod packets were then used in electric field alignment experiments.

Assembly Formation of Rods on Lithographically Defined Surfaces

Substrates to assemble rods that consist of arrays pits have been used. The pits have Au bottoms and are either 400 nm deep (for larger rods) or 100 nm deep (for 70 nm diameter rods)×2 µm×8 µm or 5 µm (respectively). The surrounding material is a polymerized benzylcyclobutene that contains Si. This polymer is then etched in oxygen plasma, leaving an $SiO_2$-like surface.

In an initial attempt to put rods in the pits, Au rods (ca. 8 µm) were left bare, and the Au pit bottoms were derivatized with 1,4 butane dithiol. The bare rods were suspended in ethanol, and the substrate was placed in this solution. After allowing to react, the still wet substrate was viewed under a light microscope. As the solvent front receded, rods were moved across the surface of the lithographic structure. Rods were observed to move into the pits and to become lodged there even as the solvent front passed over them. In a different approach to forming rod structures in pits, the BCB surface was treated with a perfluorinated silane in order to make it hydrophobic and relatively "non-stick," and the Au pit bottoms were treated with MESA. Au rods (ca. 8 µm) were coated with MESA followed by polydimethyldiallyl ammonium chloride (PDAC) to give them a permanent positive charge and render them attractive to the negatively charged pit bottoms. The rods are observed to enter the pits; however, many more rods seem to physisorb to the surface despite the perfluorination. In another attempt to create an attractive interaction between rods and the pits, the pit bottoms and the Au rods were both treated with polyethyleneglycol (PEG) and allowed to react. No useful rod-pit interaction was seen.

By eliminating the perfluorination of the BCB and allowing MESA pits and MESA/PDAC rods to interact again, an increase of rods in pits was shown. While the perfluorination provided a hydrophobic surface that would be repulsive to the aqueous, hydrophilic rods, it was ultimately more like the polymer coated rods than the water. This factor seems to have resulted in the rods being relatively attracted to the perfluorinated surface. By leaving the BCB untreated, PDAC polymer coated rods are relatively more attracted to the MESA treated pits.

In another embodiment, the surface was treated with aminopropyltrimethoxysilane (APTMS), followed by PDAC, and an overnight treatment with mercaptoethylamine (MEA). MESA/PDAC rods were used again. The rods and surfaces were allowed to react overnight. A relatively high percentage of rods are found in the pits, and other lithographically defined Au structures have a high density of rods.

Au tipped Ni rods (ca. 3 µm) derivatized with MESA/PAH were placed on MESA derivatized surfaces. The Ni rods are magnetic and may be aligned and moved with a magnetic field. The surfaces were allowed to react with the rods for several hours or overnight, and the still wet substrates were exposed to a magnetic field. The rods and rod bundles align with the field. Longer magnetic rods were available; however, they did not align with the magnetic field while on the surface.

Example 12

One embodiment of the present invention is directed to the template-directed synthesis of nanoscale electronic devices, in particular diodes. One approach, combines the membrane replication electrochemical plating of rod-shaped metal electrodes with the electroless layer-by-layer self-assembly of nanoparticle semiconductor/polymer films sandwiched between the electrodes. Described below, is the wet layer-by-layer self-assembly of multilayer $TiO_2$/polyaniline film on the top of a metal nanorod inside 200 nm pores of an alumina membrane.

1. Materials 200 nm pore diameter Whatman Anoporedisks ($Al_2O_3$-membranes) were used for template directed diode synthesis. Electrochemical metal deposition was carried out using commercially available gold (Technic Orotemp 24), platinum (Technic TP), and silver plating solutions. Titanium tetraisopropoxide[$Ti(ipro)_4$], mercaptoethylamine hydrochloride(MEA),ethyltriethoxy silane, chlorotrimethyl silane were purchased from Aldrich. All the reagents were used without further purification. All other chemicals were reagent grade and obtained from commercial sources.

$TiO_2$ colloid was prepared as follows. $Ti(ipro)_4$ was dissolved in 2-methoxyethanol under cooling and stirring. The solution was kept under stirring until it became slightly yellow, after which another portion of 2-methoxyethanol containing HCl was added. The molar ratio of the components in the prepared solution was $Ti(ipro)_4$: HCl:2-metoxyethanol=1:0.2:20. This solution was diluted with water to adjust $TiO_2$ concentration to 1% and allowed to age during 3 weeks. The resulting opalescent sol was subjected to the rotary evaporation at 60° C. to give shiny powder of xerogel containing 75% (w/w) titania. This xerogel was used as a precursor for the preparation of stock aqueous $TiO_2$ sol with $TiO_2$ concentration of 2.3% wt (0.29 M) and pH=3, which was stable during several weeks. XRD investigations of the titania xerogel allowed estimating average size of the colloidal anatase crystals at 6 nm, TEM image of the stock $TiO_2$ sol shows particles of a 4–13 nm in diameter.

The emmeraldine base (EB) form of polyaniline (PAN) was also prepared. A dark blue solution of PAN in dimethyl formamide (0.006% wt) was used as a stock solution for the film synthesis.

2. Synthesis of rod-shaped diodes

The synthesis of rod-shaped diodes was carried out as follows. Metal electrodes were grown electrochemically inside porous membrane. Briefly, the membrane was pretreated by evaporating ~150 nm of silver on its branched side. To completely fill the pores on this side 1 C of silver was electroplated onto the evaporated silver. These Ag "plugs" were used as foundations onto which a bottom electrode was electrochemically grown. The bottom gold electrode of desired length was electroplated sonicating. The plating solution was removed by soaking the membrane in water and drying in Ar stream. Priming the bottom electrode surface with MEA preceded depositing multilayer $TiO_2$/PAN film. This was achieved by 24 hour adsorption from MEA(5%) ethanolic solution. The multilayer film was grown by repeating successive immersing the membrane in the $TiO_2$ aqueous solution and PAN solution in DMF for 1 h. Each adsorption step was followed by removing the excess of reagents by soaking the membrane in several portions of an appropriate solvent (0.01 M aqueous HCl or DMF) for 1 h, and drying in Ar stream. Finally, a top electrode (Ag or Pt) of desired length was electroplated at the top of $TiO_2$MAN multilayer without sonicating. Then the evaporated silver, Ag "plugs" and alumina membrane were removed by dissolving in 6 M nitric acid and 0.5M NaOH, respectively. (2–4 C of Au was always electroplated on the top of Ag electrode to prevent dissolving the latter in the nitric acid. Also preliminary experiments showed that multilayer $TiO_2$/PAN film self-assembled on plane Au(MEA) substrate did not destroy in the 0.5 M NaOH.) The resulting rod-shaped diodes were repeatedly centrifuged and washed with water.

In most of the experiments, chemical passivation of $Al_2O_3$-membrane pore walls was applied using treatments with propionic acid (20 had sorption from 0.0013 M aqueous solution) or alkylsilane derivatives. In the latter case, a membrane was successively soaked in absolute ethanol andanhydrous toluene or dichlorethane for 1 h, after which it was immersed in a ethyltriethoxy silane solution in anhydrous toluene (2.5% vol) or a chlorotrimethyl silane solution in anhydrous dichlorethane (2.5% vol) for 15 h. Then the membrane was successively soaked for 1 h in the appropriate anhydrous solvent, a mixture (1:1) of the solvent and absolute ethanol, the absolute ethanol, and finally was dried in Ar stream. Wetting so treated membranes with water revealed hydrophobic properties of their external surface. Transmission IR spectra of the membrane treated with ethyltriethoxy silane or propionic acid showed the appearance of weak bands at 2940, 2865, 2800 cm-1, which can be assigned to C—H stretching vibrations of alkyl and alkoxy groups.

3. Characterization

Transmission electron microscope (TEM) images were obtained with a JEOL 1200 EXII at 120 kV of accelerating voltage and 80 mA of filament current. Optical microscope (OM)images were recorded. Transmission IR spectra were recorded using a Specord M-80 CareZeiss Jena spectrometer. I–V characteristics for rod-shaped diodes were measured in air at ambient temperature.

TEM images of some typical "striped" bimetallic Au/Pt/Au nanorods, grown electrochemically inside the porous alumina membrane, showed that the two rod ends differed in their topography—one of the rod ends appeared to be bulging or rounded while the other rod end had an apparent hollow in the middle. Such differences in rod end appearance could be explained by adsorption of some amount of metal ions on pore walls, promoting metal (e.g. Ag) growth in the near-wall space and causing the hollow formation in the pore middle space. During the electroplating of a second metal "stripe" (e.g. Au), the growing metal follows the surface of the bottom rod and fills the hollow thus forming the rounded end. Further rod growth results in a cup-like end due to the metal adsorption on the pore walls. Each sequential metal segment grows in the same way in the end of the underlying segment.

It is unlikely that the relatively rough surface on the top end of a rod may be completely covered with the ultrathin $TiO_2$/PAN film thus preventing immediate contacts between bottom and top metal electrodes. From preliminary experiments on plane Au-substrates, it was found that the multilayer $TiO_2$/PAN films grown on smoother surfaces demonstrated better reproducibility in their rectifying behavior. Passivation (hydrophobization) of $Al_2O_3$-terminated surface of pore walls with propionic acid or alkylsilane derivatives, such as ethyltriethoxy silaneor chlorotrimethyl silane, was tried to smooth down the top rod end surface by reducing the metal adsorption on the pore walls. The hydrophobization of pore walls may also be expected to prevent $TiO_2$ particles from adsorption on the wall surface rather than on metal electrode surface situated in the depth (~65 mm) of the pore. It was shown that the $TiO_2$ particles readily formed a densely packed layer on a plane $Al/Al_2O_3$ substrate. A typical higher resolution image of rod's upper part confirmed that the cup-like ends are situated at the top of the rods, and showed that the wall passivation to some extent resulted in smoothing of the surface of rod ends.

An optical micrograph of Au/($TiO_2$/PAN)$_{10}$/Ag/Au rods, prepared using the membrane derivatized with ethyltriethoxy silane, showed nanorods of uniform length, in which a silver segment is clearly seen between two gold ends. TEM images of such a rod, recorded in the first several seconds, revealed no visible signs of a metal/film/metal heterojunction within the rod. However, after focusing the electron beam on this rod for some time (typically tens of seconds), a break appeared in the rod and metal segments became separated, perhaps due to beam-induced metal melting, in the neighborhood of the Au/film/Ag heterojunction. In higher resolution TEM images of this break, particles of 5–10 nm in diameter, which adhere to both metal ends, were observed. Apparently, $TiO_2$ nanoparticles are present between two electroplated metals. The OM and TEM data suggest that the self-assembly of multilayer $TiO_2$/PAN film on the Au rod top can be realized inside the membrane pores, and that the self-assembled film does not prevent Ag rod electroplating on the top of the film. It should be noted that TEM images in all likelihood do not give a true picture of the multilayer $TiO_2$/PAN film inside the rod because of high probability of the mechanical film destruction while separating partially melted metal rod ends. Longer time exposure of the rod to the electron beam causes complete destruction of the heterojunction and arising two individual nanorods with nanoparticles stuck to their ends.

In order to investigate multilayer $TiO_2$/PAN film sandwiched between Au and Ag rods, Au/($TiO_2$/PAN)$_6$/Ag nanorods were prepared and their top Ag electrode was dissolved in nitric acid. The remaining 2 C Au rods with ($TiO_2$/PAN)$_6$ film deposited on their top were analyzed by TEM. Preliminary studies showed that ellipsometric thickness of multilayer $TiO_2$/PAN film self-assembled on plane Au(MEA) substrate did not decrease after immersion in 6 M $HNO_3$ for 30 min suggesting stability of the film in the acidic medium. Furthermore, similar to the Au/($TiO_2$/PAN)$_{10}$/Ag/Au rods described above, TEM image of the Au/($TiO_2$/PAN)$_6$ rod taken in the first several seconds did not reveal any particles. However, during longer exposure to the electron beam, gold melted revealing nanoparticle film on the rod's top. It can be seen that the upper contour line of the film is very close to that of Au rod before melting. This fact is consistent with the cup-shaped top of the metal rods. The multilayer film grows on the surface both of cup bottom and cup walls and approximately retains cup shape after the thin walls have melted. This explanation is consistent with observed film height of ~100 nm, which allows estimating rather gold cup depth than ($TiO_2$/PAN)$_6$ film thickness. Ellipsometric thickness of $TiO_2$/PAN)$_6$ film self-assembled on a plane Au(MEA) substrate is estimated at about 10 nm.

I–V characteristic of the Pt/($TiO_2$/PAN)$_3$ $TiO_2$/Au rod-shaped device reveals current rectifying behavior. The forward and reverse bias turn-on potentials are ~−0.2 and ~0.9 V, respectively.

We claim:

1. A freestanding rod-shaped particle comprising 2 to 50 segments, wherein the particle has a generally circular cross-section along its length, wherein the segment transitions are generally perpendicular to said length, wherein the particle length is from 20 nm to 50 µm and the particle width is from 5 nm to 50 µm, and
   wherein at least one segment is comprised of a metal selected from the group consisting of: silver, gold, copper, nickel, palladium, platinum, cobalt, rhodium and iridium, and wherein the particle contains information regarding an associated material.

2. The particle of claim 1, wherein the particle length is from 500 nm–30 µm.

3. The particle of claim 1, wherein the particle length is from 1–15 µm.

4. The particle of claim 1, wherein the particle width is from 10 nm–2 µm.

5. The particle of claim 1, wherein the particle width is from 30 nm to 500 nm.

6. The particle of claim 1, comprised of 2–10 different types of segments.

7. The particle of claim 1, wherein the lengths of said segments is from 1 nm to 50 µm.

8. The particle of claim 1, wherein the length of at least one of said segments is from 50 nm to 15 µm.

9. The particle of claim 1, wherein the particle length is from 1–15 µm width is from 30 nm to 2 µm, and the lengths of at least one of said segments are from 50 nm to 15 µm.

10. The particle of claim 1, wherein the particle length is from 1–15 µm, the particle width is from 2 µm to 50 µm, and the lengths of said segments are from 50 nm to 15 µm.

11. A freestanding segmented rod-shaped particle manufactured by a method including the deposition of a plurality of materials inside a template, the method of manufacturing the particle comprising:
   a) causing deposition of a first material into a pore of said template;
   b) causing deposition of a second material into said pore of said template, wherein the deposition of at least one of said first material and said second material is electrochemical deposition; and c) releasing said segmented particle from said template to provide a freestanding segmented particle having a length from 10 nm to 50 μm and a width from 5 nm to 50 μm, wherein said particle has a generally circular cross-section along its length, wherein the segment transitions are generally perpendicular to said length, and wherein the particle comprises 50 or fewer segments, and wherein at least one of said segments has a length of at least 10 nm, and wherein the particle contains information regarding an associated material.

12. The particle of claim 11, wherein the particle length is from 500 nm–30 μm.

13. The particle of claim 11, wherein the particle length is from 1–15 μm.

14. The particle of claim 11, wherein the particle width is from 10 nm–2 μm.

15. The particle of claim 11, wherein the particle width is from 30 nm to 500 nm.

16. The particle of claim 11, comprised of 2–10 different types of segments.

17. The particle of claim 11, wherein the lengths of said segments is from 1 nm to 50 μm.

18. The particle of claim 11, wherein the lengths of at least one of said segments is from 50 nm to 15 μm.

19. The particle of claim 11, wherein the particle length is from 1–15 μm, the particle width is from 30 nm to 2 μm, and the length of at least one of said segments are from a 50 nm to 15 μm.

20. A freestanding particle comprising 2 to 50 segments, wherein the particle length is from 20 nm to 50 μm, and the particle width is from 5 nm to 50 μm, and wherein at least one of said segments is comprised of a superparamagnetic compound.

21. A freestanding rod-shaped particle comprising 2 to 50 segments, wherein the particle has a generally circular cross-section along its length, wherein the segment transitions are generally perpendicular to said length, wherein the particle length is from 20 nm to 50 μm, and the particle width is from 5 mm to 50 nm, wherein at least one segment is comprised of a metal selected from the group consisting of: silver, gold, copper, nickel, palladium, platinum, cobalt, rhodium and iridium; and wherein the particle is an electronic device or a part of an electronic device.

22. The particle of claim 21 wherein said electronic device or part of an electronic device is selected from the group consisting of a conductor, or diode, a transistor, a wire, a capacitor, a resistor, a negative differential resistance device, a resonant tunneling diode, a ferroelectric switch, a shift register and a delay line.

* * * * *